United States Patent [19]
Jegham et al.

[11] Patent Number: 5,641,785
[45] Date of Patent: Jun. 24, 1997

[54] OXAZOLOQUINOLINONE DERIVATIVES, THEIR PREPARATION AND THEIR THERAPEUTIC APPLICATION AS INHIBITORS OF MONOAMINE OXIDASE

[75] Inventors: Samir Jegham, Argenteuil; Jean Jacques Koenig, Maisons Laffitte; Frederic Puech, Rueil Malmaison; Philippe Burnier, Maisons Laffitte; Lydia Zard, Gif sur Yvette, all of France

[73] Assignee: Synthelabo, Le Plessis Robinson, France

[21] Appl. No.: 523,508

[22] Filed: Sep. 1, 1995

[30] Foreign Application Priority Data

Sep. 5, 1994 [FR] France .................. 94 10600

[51] Int. Cl.⁶ .................. A61K 31/44; C07D 498/02
[52] U.S. Cl. .................. 514/291; 546/92
[58] Field of Search .................. 546/92; 514/291

[56] References Cited

U.S. PATENT DOCUMENTS

| | | | |
|---|---|---|---|
| 5,001,129 | 3/1991 | Renaud et al. | 514/291 |
| 5,130,327 | 7/1992 | Alvarez | 514/415 |
| 5,356,916 | 10/1994 | Toyofuku | 514/364 |

*Primary Examiner*—C. Warren Ivy
*Assistant Examiner*—Evelyn Huang
*Attorney, Agent, or Firm*—Jacobson, Price, Holman & Stern, PLLC

[57] ABSTRACT

3,3a,4,5-Tetrahydro-1H-oxazolo[3,4-a]quinolin-1-one derivatives of formula (I)

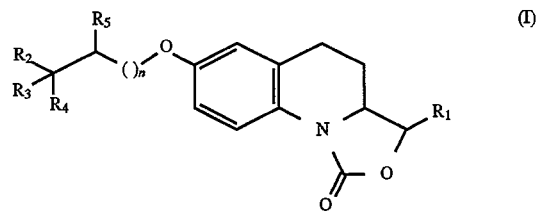

in which:

n is 0 or 1, $R_1$ represents a hydrogen atom or an ethenyl, methyl, ethyl, phenyl, hydroxymethyl or methoxymethyl group, and (i) $R_2$ is a methyl, trifluoromethyl or cyano group, $R_3$ is a hydrogen atom or a hydroxyl or benzyloxy group and $R_4$ and $R_5$ are hydrogen atoms, or (ii) $R_2$ and $R_4$ together form a —$(CH_2)_4$— group, $R_3$ is a hydroxyl group and $R_5$ is a hydrogen atom, or (iii) $R_2$ and $R_5$ together form an —O—$(CH_2)_3$— group, and $R_3$ and $R_4$ are hydrogen atoms, or (iv) $R_2$ and $R_5$ together form a —$(CH_2)_4$ group, $R_3$ is a hydroxyl group and $R_4$ is a hydrogen atom, are useful as selective inhibitors of MAO-A or as mixed inhibitors of MAO-A and MAO-B.

8 Claims, No Drawings

OXAZOLOQUINOLINONE DERIVATIVES, THEIR PREPARATION AND THEIR THERAPEUTIC APPLICATION AS INHIBITORS OF MONOAMINE OXIDASE

The present invention relates to 3,3a,4,5-tetrahydro-1H-oxazolo[3,4-a]quinolin-1-one derivatives, to their preparation and to their therapeutic application.

3,3a,4,5-Tetrahydro-1H-oxazolo[3,4-a]quinolin-1-one derivatives, which are useful as antidepressants, are known from EP-B-322,263.

The present invention provides a 3,3a,4,5-tetrahydro-1H-oxazolo[3,4-a]quinolin-1-one derivative of formula (I)

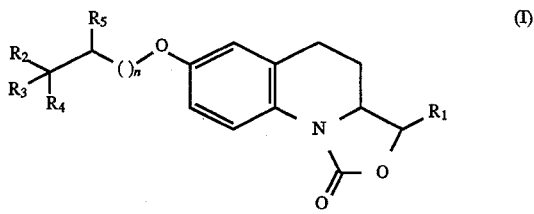

in which:

n is 0 or 1, $R_1$ represents a hydrogen atom or an ethenyl, methyl, ethyl, phenyl, hydroxymethyl or methoxymethyl group, and
  (i) $R_2$ is a methyl, trifluoromethyl or cyano group, $R_3$ is a hydrogen atom or a hydroxyl or benzyloxy group and $R_4$ and $R_5$ are hydrogen atoms,
  or (ii) $R_2$ and $R_4$ together form a —(CH$_2$)$_4$— group, $R_3$ is a hydroxyl group and $R_5$ is a hydrogen atom,
  or (iii) $R_2$ and $R_5$ together form an —O—(CH$_2$)$_3$— group, and $R_3$ and $R_4$ are hydrogen atoms,
  or (iv) $R_2$ and $R_5$ together form a —(CH$_2$)$_4$ group, $R_3$ is a hydroxyl group and $R_4$ is a hydrogen atom, in the form of an isomer or a mixture of isomers.

The compounds of the invention may exist in various isomeric forms, including enantiomeric and diastereoisomeric forms. The present invention comprises these various forms as well as the mixtures thereof, including racemic mixtures.

The present invention also provides a process for the preparation of a derivative of formula (I) (see also Annex 1), in which a compound of formula (II)

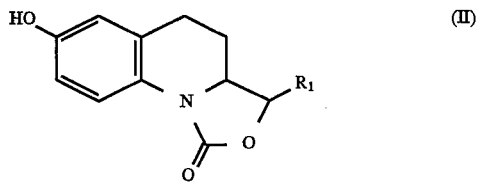

in which $R_1$ represents a hydrogen atom or an ethenyl, methyl, phenyl, hydroxymethyl or methoxymethyl group, is treated with a compound of formula (III)

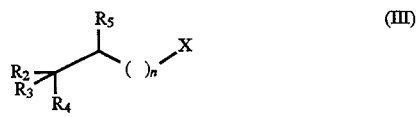

in which n, $R_2$, $R_3$, $R_4$ and $R_5$ are defined as in formula (I) and X represents a halogen atom or a labile group such as mesyloxy or tosyloxy, to obtain a derivative of formula (I) in which $R_1$ is defined as above, and, if desired, reducing the derivative of formula (I) in which $R_1$ is an ethenyl group, to obtain a derivative of formula (I) in which $R_1$ is an ethyl group.

The compounds of formula (II) in which $R_1$ represents a hydrogen atom or an ethenyl, methyl or phenyl group may be prepared from ethyl 2-formyl-6-methoxy-1,2,3,4-tetrahydroquinoline-1-carboxylate, a known compound whose preparation is described in EP-B-322,263.

In the case where $R_1$ is a hydrogen atom, this process consists in treating ethyl 2-formyl-6-methoxy-1,2,3,4-tetrahydroquinoline-1-carboxylate with a reducing agent such as sodium borohydride or potassium borohydride, in cyclizing the compound obtained, by reaction with a base such as sodium methoxide, and, finally, in demethylating the 7-methoxy-3,3a,4,5-tetrahydro-1H-oxazolo[3,4-a]quinolin-1-one of formula (IV)

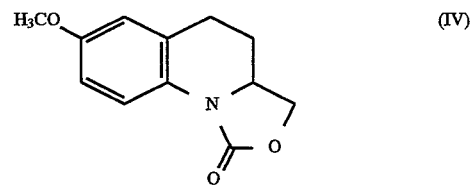

In the case where $R_1$ is an ethenyl, methyl or phenyl group, this process consists in treating ethyl 2-formyl-6-methoxy-1,2,3,4-tetrahydroquinoline-1-carboxylate with an organomagnesium compound of formula $R_1MgX$, in which $R_1$ represents an ethenyl, methyl or phenyl group and X represents a halogen atom, in cyclizing the compound obtained, by reaction with a base such as sodium methoxide, and, finally, in demethylating the 7-methoxy-3,3a,4,5-tetrahydro-1H-oxazolo[3,4-a]quinolin-1-one derivative of formula (V)

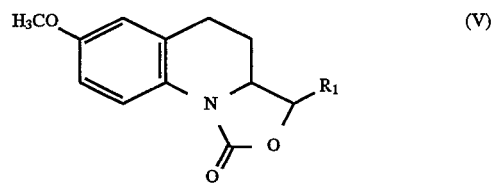

in which $R_1$ is defined as above.

The compounds of formula (II) in which $R_1$ represents a hydroxymethyl or methoxymethyl group may be prepared from 3-ethenyl-7-hydroxy-3,3a,4,5-tetrahydro-1H-oxazolo[3,4-a]quinolin-1-one, a compound of formula (II) in which $R_1$ represents an ethenyl group, by protection of the hydroxyl group in order to obtain a compound of formula (VI)

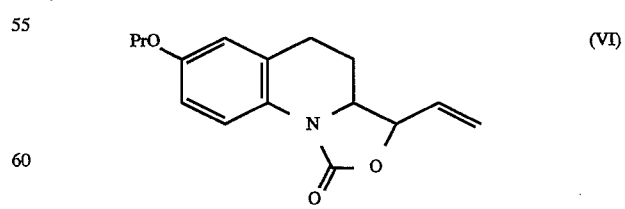

in which Pr represents a protecting group such as benzyl, which compound is then treated with ozone and then with a reducing agent, such as sodium borohydride, in order to give a compound of formula (VII)

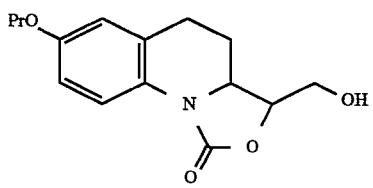

(VII)

which is either deprotected in order to give a compound of formula (II) in which $R_1$ is a hydroxymethyl group, or treated with dimethyl sulphate in order to give a compound of formula (VIII)

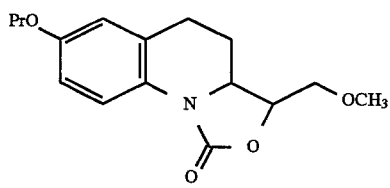

(VIII)

which is then deprotected in order to give the compound of formula (II) in which $R_1$ represents a methoxymethyl group.

The compounds of formula (I) in which $R_1$ represents an ethenyl, methyl, ethyl, phenyl, hydroxymethyl or methoxymethyl group exist in the form of cis and trans isomers

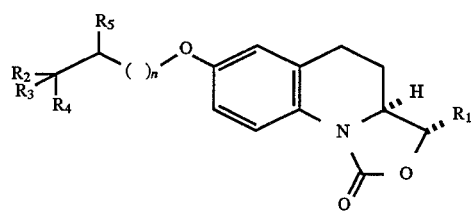

(I cis)

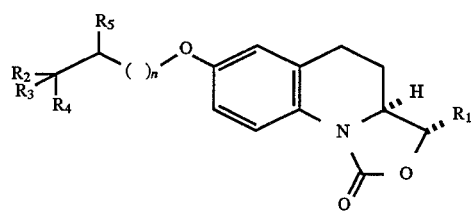

(I trans)

which are respectively prepared from the cis and trans isomers of the corresponding compounds of formula (II), which are themselves obtained according to the process as described above, after separation by chromatography of the cis and trans isomers of the derivative of formula (V)

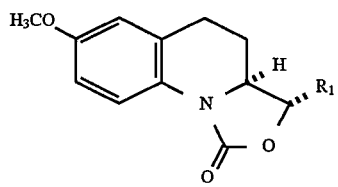

(V cis)

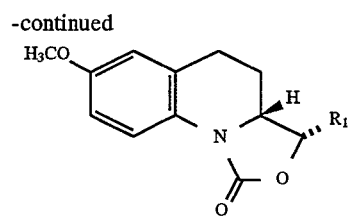

(V trans)

The compounds of formula (I), in which $R_1$ is an ethenyl group and $R_3$ a benzyloxy group, or alternatively $R_1$ is a hydroxymethyl or methoxymethyl group and $R_3$ a hydroxyl or benzyloxy group, $R_4$ and $R_5$ are hydrogen atoms and $R_2$ and n are defined as in formula (I), may also be prepared according to the process represented in Annex 2, which consists in treating 3-ethenyl-7-hydroxy-3,3a,4,5-tetrahydro-1H-oxazolo[3,4-a]quinolin-1-one, a compound of formula (II) in which $R_1$ represents an ethenyl group, with a compound of formula $R_2CH(OH)—(CH_2)—(CH_2)_nX$, in which $R_2$ and n are defined as above and X is a halogen atom or a labile group, such as tosyloxy or mesyloxy, in treating the compound obtained, of formula (IX)

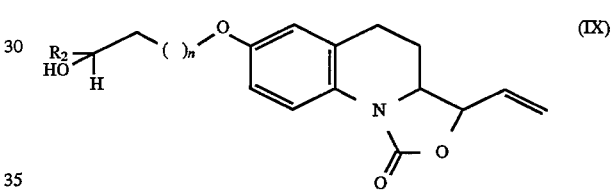

(IX)

with a benzyl halide, in reacting the compound obtained, of formula (X)

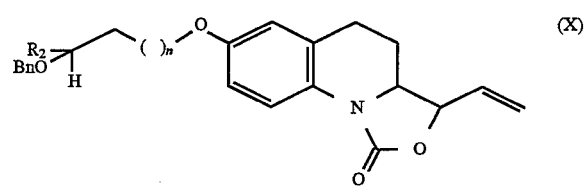

(X)

with ozone and then with a reducing agent such as sodium borohydride, in order to obtain the derivative of formula (XI)

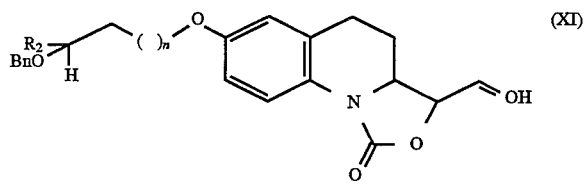

(XI)

which is then either deprotected in order to give the corresponding compound of formula (I), in which $R_1$ is a hydroxymethyl group and $R_3$ a hydroxyl group, or treated with dimethyl sulphate in order to give the compound of formula (XII)

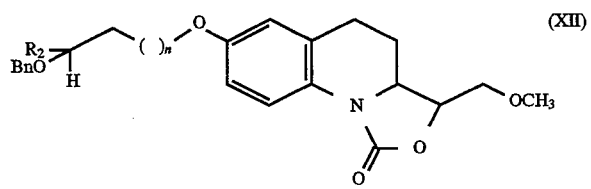

which is then deprotected in order to give the corresponding compound of formula (I), in which $R_1$ is a methoxymethyl group and $R_3$ is a hydroxyl group.

The enantiomers and diastereoisomers of the compounds of formula (I) are prepared from the enantiomers or diastereoisomers of the compounds of formula (II) and/or from the enantiomers of the compounds of formula (III).

The enantiomers and diastereoisomers of the compounds of formula (II) are themselves obtained from the enantiomers and diastereoisomers of the compounds of formula (IV) or (V), which are prepared from racemic ethyl 6-methoxy-2-methoxycarbonyl-1,2,3,4-tetrahydroquinoline-1-carboxylate, according to the process represented in Annex 3.

This process comprises the separation, by enzymatic hydrolysis, of the enantiomers of ethyl 6-methoxy-2-methoxycarbonyl-1,2,3,4-tetrahydroquinoline-1-carboxylate, consisting in treating the racemic compound in a buffer solution such as a mixture of potassium dihydrogen phosphate and disodium phosphate or in a two-phase medium such as toluene/buffer solution, with an enzymatic extract such as pig liver esterase, horse, pig, bovine or rabbit liver acetone powders and, more particularly, sheep liver acetone powder (marketed by Sigma), and in separating, by extraction, ethyl S-(−)-6-methoxy-2-methoxycarbonyl-1,2,3,4-tetrahydroquinoline-1-carboxylate from ethyl R-(+)-2-carboxy-6-methoxy-1,2,3,4-tetrahydroquinoline-1-carboxylate.

When ethyl R-(+)-2-carboxy-6-methoxy-1,2,3,4-tetrahydroquinoline-1-carboxylate is treated with thionyl chloride in a solvent such as toluene, and then with methanol, it gives ethyl R-(+)-6-methoxy-2-methoxycarbonyl-1,2,3,4-tetrahydroquinoline-1-carboxylate.

When ethyl R-(+)- and S-(−)-6-methoxy-2methoxycarbonyl-1,2,3,4-tetrahydroquinoline-1-carboxylate are treated with lithium borohydride, they lead respectively to the R-(−) and S-(+) enantiomers of 7-methoxy-3,3a,4,5-tetrahydro-1H-oxazolo-[3,4-a]quinolin-1-one (IV).

When ethyl R-(+)- and S-(−)-6-methoxy-2-methoxycarbonyl-1,2,3,4-tetrahydroquinoline-1-carboxylate are treated with diisobutylaluminium hydride in a solvent such as toluene, they lead respectively to ethyl R-(+)- and S-(−)-2-formyl-6-methoxy-1,2,3,4-tetrahydroquinoline-1-carboxylate which, on reaction with an organomagnesium compound of formula $R_1MgX$ in which $R_1$ represents an ethenyl, methyl or phenyl group and X represents a halogen atom, in a solvent such as tetrahydrofuran, followed by a reaction with sodium methoxide in a solvent such as toluene and then chromatographic separation, give, on the one hand, the (−) diastereoisomers of configuration [3(R),3a(R)] and [3(S),3a(R)], and, on the other hand, the (+) diastereoisomers, of configuration [3(S),3a(S)] and [3(R),3a(S)], of the compounds of formula (V).

Racemic ethyl 6-methoxy-2-methoxycarbonyl-1,2,3,4-tetrahydroquinoline-1-carboxylate, used as starting material, may be prepared by reaction of 6-methoxyquinoline with potassium cyanide or trimethylsilyl cyanide and benzoyl chloride, in a solvent such as dichloromethane, reaction of the 1-benzoyl-2-cyano-6-methoxy-1,2-dihydroquinoline obtained with hydrobromic acid in acetic acid, then with aqueous ammonia and finally with acetic acid, treatment of the 2-carboxy-6-methoxyquinoline obtained with thionyl chloride in a solvent such as toluene, and then with methanol, in order to obtain 6-methoxy-2-methoxycarbonylquinoline, which is reduced with hydrogen in the presence of platinum oxide and hydrochloric ethanol in methanol, in order to give 6-methoxy-2-methoxycarbonyl-1,2,3,4-tetrahydroquinoline, which is then treated with ethyl chloroformate in a solvent such as dichloromethane, in the presence of potassium carbonate.

The examples which follow illustrate the present invention.

EXAMPLE 1

[3α,3aβ,7(R)]-3-ethenyl-7-[4,4,4-trifluoro-3-hydroxybutoxy]-3,3a,4,5-tetrahydro-1H-oxazolo[3, 4-a]quinolin-1-one 1.1 cis- and trans-(±)-3-Ethenyl-7-methoxy-3,3a,4,5-tetrahydro-1H-oxazolo[3,4-a]quinolin-1-one To a solution of 116.3 g (0.442 mol) of ethyl 2-formyl-6-methoxy-1,2,3,4-tetrahydroquinoline-1-carboxylate in 800 ml of tetrahydrofuran, cooled to −30° C. and with stirring, are added, under argon and over 30 min, 486 ml (0.486 mol) of 1M vinylmagnesium bromide. The reaction medium is left stirring for 2 h, followed by addition of chilled saturated aqueous ammonium chloride solution. The mixture is extracted twice with ethyl acetate, the extracts are washed with water, dried over sodium sulphate and the solvent is evaporated off under reduced pressure. The residual oil is redissolved in 340 ml of toluene and heated to reflux in order to remove the traces of water. 1 ml of 10% sodium methoxide solution in methanol is then added, at 90° C., and the mixture is again heated at reflux, while distilling off the ethanol formed. The mixture is evaporated to dryness, the residue is taken up in ethyl acetate and washed with water, then the organic phase is dried over sodium sulphate and the solvent is evaporated off under reduced pressure. By chromatography of the product on a column of silica with a 4/1 mixture of heptane and ethyl acetate, 32.9 g of trans derivative (melting point: 100° C.) and 13.4 g of cis derivative (melting point: 134° C.) are obtained.

1.2. trans-(±)-3-Ethenyl-7-hydroxy-3,3a,4,5-tetrahydro-1H-oxazolo[3,4-a]quinolin-1-one To a solution of 24.6 g (0.1 mol) of trans-(±)-3-ethenyl-7-methoxy-3,3a,4,5-tetrahydro-1H-oxazolo[3,4-a]quinolin-1-one in 280 ml of dichloromethane are added dropwise, at 0° C., 19 ml (0.20 mol) of boron tribromide, and, after 1 h, saturated aqueous sodium bicarbonate solution is then run in to the point of neutrality. The mixture is filtered and the filtrate is then extracted with dichloromethane containing 10% of methanol. The organic phase is washed with water and dried over sodium sulphate, and the solvent is then evaporated off under reduced pressure. The solid residue is then triturated in a 1/1 mixture of dichloromethane and methanol. It is filtered and dried to obtain finally 21.4 g of product.

Melting point: 216° C.

Starting with cis-(±)-3-ethenyl-7-methoxy-3,3a,4,5-tetrahydro-1H-oxazolo[3,4-a]quinolin-1-one, cis-(±)-3-ethenyl-7-hydroxy-3,3a,4,5-tetrahydro-1H-oxazolo[3,4-a]quinolin-1-one was obtained.

Melting point: 250° C.

1.3. [3α,3aβ,7(R)]-3-Ethenyl-7-[4,4,4-trifluoro-3-hydroxybutoxy]-3,3a,4,5-tetrahydro-1H-oxazolo[3,4-a]quinolin-1-one To a solution of 21.2 g (0.092 mol) of trans-(±)-3-ethenyl-7-hydroxy-3,3a,4,5-tetrahydro-1H-oxazolo[3,4-a]quinolin-1-one in 150 ml of acetonitrile are added, under argon and at room temperature, 25.4 g (0.183 mol) of potassium carbonate and then 34.9 g (0.138 mol) of 1-iodo-3(R)-hydroxy-4,4,4-trifluorobutane. After 4 h, the mixture is diluted with dichloromethane and washed with water. The organic phase is dried over sodium sulphate and the solvent is then evaporated off under reduced pressure. The residual oil is purified by chromatography on a column of silica, with chloroform containing 0 to 3% of methanol. After crystallization from an acetone/diisopropyl ether mixture, 30 g of product are obtained.

Melting point: 135.8° C.

EXAMPLE 2

[3α,3aβ,7(R)]-3-Hydroxymethyl-7-[4,4,4-trifluoro-3-benzyloxybutoxy]-3,3a,4,5-tetrahydro-1H-oxazolo[3,4-a]quinolin-1-one 2.1. [3α,3aβ,7(R)]-3-Ethenyl-7-[4,4,4-trifluoro-3-benzyloxybutoxy]-3,3a,4,5-tetrahydro-1H-oxazolo[3,4-a]quinolin-1-one To a solution of 30.0 g (840 mmol) of [3α,3aβ,7(R)]-3-ethenyl-7-[4,4,4-trifluoro-3-hydroxybutoxy]-3,3a,4,5-tetrahydro-1H-oxazolo[3,4-a]quinolin-1-one in 300 ml of toluene are added a solution of 13.4 g of sodium hydroxide in 13.4 ml of water, 2.7 g (8.4 mmol) of tetrabutylammonium bromide and then 43.1 g (0.252 mol) of benzyl bromide. The mixture is stirred for 2 h at room temperature and then extracted with ethyl acetate, washed with water and dried over sodium sulphate, and the solvent is evaporated off under reduced pressure. The oily residue is purified by chromatography on a column of silica, with a 1/1 mixture of heptane and chloroform. 35 g of product are obtained in the form of an oil.

2.2. [3α,3aβ,7(R)]-3-Hydroxymethyl-7-[4,4,4-trifluoro-3-benzyloxybutoxy]-3,3a,4,5-tetrahydro-1H-oxazolo[3,4-a]quinolin-1-one Ozone is sparged for 3 h, at −30° C., into a solution of 31.5 g (70.4 mmol) of [3α,3aβ,7(R)]-3-ethenyl-7-[4,4,4-trifluoro-3-benzyloxybutoxy]-3,3a,4,5-tetrahydro-1H-oxazolo[3,4-a]quinolin-1-one in 515 ml of dichloromethane and 780 ml of methanol. The ozone is then stripped off by flushing with a stream of nitrogen, and 26.8 g (0.704 mol) of sodium borohydride are added while maintaining the temperature at −30° C. After 5 min, 21.8 g (0.352 mol) of dimethyl sulphide are added and the mixture is allowed to return to room temperature. It is then washed with water, the organic phase is dried over sodium sulphate and the solution is concentrated under reduced pressure. The product obtained is purified by chromatography on a column of silica, with dichloromethane containing 0 to 5% of methanol. After recrystallization from diethyl ether, 26.5 g of product are obtained.

Melting point: 111.6° C.

EXAMPLE 3

[3α,3aβ,7(R)]-3-Methoxymethyl-7-[4,4,4-trifluoro-3-benzyloxybutoxy]-3,3a,4,5-tetrahydro-1H-oxazolo[3,4-a]quinolin-1-one To a solution of 7.8 g (17 mmol) of [3α,3aβ,7(R)]-3-hydroxymethyl-7-[4,4,4-trifluoro-3-benzyloxybutoxy]-3,3a,4,5-tetrahydro-1H-oxazolo[3,4-a]quinolin-1-one in 85 ml of toluene are added 0.54 g (1.7 mmol) of tetrabutylammonium bromide and then 6.4 g (51 mmol) of dimethyl sulphate. A solution of 2.7 g (67 mmol) of sodium hydroxide in 2.7 ml of water is then added dropwise over 30 min. The reaction medium is stirred for 30 min and then diluted with ethyl acetate, the organic phase is extracted, washed with water and dried over sodium sulphate, and the solvent is evaporated off under reduced pressure. By chromatography on a column of silica, with a 1/1 mixture of heptane and ethyl acetate, 6.2 g of product are isolated in the form of an oil.

EXAMPLE 4

[3α,3aβ,7(R)]-3-Methoxymethyl-7-[4,4,4-trifluoro-3-hydroxybutoxy]-3,3a,4,5-tetrahydro-1H-oxazolo[3,4-a]quinolin-1-one 2.8 g (6 mmol) of [3α,3aβ,7(R)]-3-methoxymethyl-7-[4,4,4-trifluoro-3-benzyloxybutoxy]-3,3a,4,5-tetrahydro-1H-oxazolo[3,4-a]quinolin-1-one are hydrogenated for 16 h in 30 ml of ethanol, in the presence of traces of hydrochloric acid and 0.6 g of 10% palladium-on-charcoal containing 50% of water. The mixture is filtered on silica and the solvent is evaporated off under reduced pressure. The product obtained is purified by chromatography on a column of silica, with a 1/1 mixture of heptane and ethyl acetate. After recrystallization from diethyl ether, 1.4 g of product are obtained.

Melting point: 94.8° C.

EXAMPLE 5

[3α,3aβ,7(S)]-7-(3-Hydroxybutoxy-3-hydroxymethyl-3,3a,4,5-tetrahydro-1H-oxazolo[3,4-a]quinolin-1-one 5.1. trans-7-Benzyloxy-3-ethenyl-3,3a,4,5-tetrahydro-1H-oxazolo[3,4-a]quinolin-1-one To a mixture of 10 g (0.043 mol) of trans-3-ethenyl-7-hydroxy-3,3a,4,5-tetrahydro-1H-oxazolo[3,4-a]quinolin-1-one (obtained in Step 2 of Example 1) and 12 g (0.086 mol) of potassium carbonate in 250 ml of acetonitrile and 50 ml of dimethylformamide are added 8.9 g (0.052 mol) of benzyl bromide. The mixture is stirred at 80° C. for 1 h then filtered while hot and washed with acetonitrile, and the filtrate is evaporated to dryness under reduced pressure. The residue is taken up in ethyl acetate and washed several times with water, and the organic phase is then dried over sodium sulphate and concentrated under reduced pressure. After recrystallization from diisopropyl ether, 12.8 g of product are obtained.

Melting point: 96° C.

5.2. trans-7-Benzyloxy-3-hydroxymethyl-3,3a,4,5-tetrahydro-1H-oxazolo[3,4-a]quinolin-1-one Ozone is sparged for 3 h 30 min into a solution of 12.5 g (0.039 mol) of trans-7-benzyloxy-3-ethenyl-3,3a,4,5-tetrahydro-1H-oxazolo[3,4-a]quinolin-1-one in 450 ml of dichloromethane and 350 ml of methanol, cooled to −40° C. The excess ozone is then stripped off with a stream of nitrogen, 14.8 g (0.39 mol) of sodium borohydride are added in small portions, followed by 12.6 g (0.195 mol) of dimethyl sulphide, and the mixture is left overnight at room temperature. It is extracted twice with dichloromethane, the organic phase is washed with water and then with saturated sodium chloride solution and dried, and the solvent is evaporated off under reduced pressure. After purification by chromatography on a column of silica, with a 95/5 mixture of dichloromethane and methanol, 10.9 g of product are obtained.

Melting point: 144° C.

5.3. trans-7-Hydroxy-3-hydroxymethyl-3,3a,4,5-tetrahydro-1H-oxazolo[3,4-a]quinolin-1-one 3.0 g (9.2 mmol) of trans-7-benzyloxy- 3-hydroxymethyl-3,3a,4,5-tetrahydro-1H-oxazolo[3,4-a]quinolin-1-one, dissolved in 20 ml of ethanol and 40 ml of tetrahydrofuran, are hydrogenated for 1 h in the presence of 1 g of 10% palladium-on-charcoal containing 50% of water. The mixture is then filtered on silica and the solvent is evaporated off under reduced pressure. 1.1 g of product are obtained.
Melting point: 250° C.

5.4. [3α,3aβ,7(S)]-7-(3-Hydroxybutoxy)-3-hydroxymethyl-3,3a,4,5-tetrahydro-1H-oxazolo[3,4-a]quinolin-1-one To a solution of 500 mg (2.13 mmol) of trans-7-hydroxy-3-hydroxymethyl-3,3a,4,5-tetrahydro-1H-oxazolo[3,4-a] quinolin-1-one in 3 ml of acetonitrile and 2 ml of dimethylformamide are added 590 mg (4.26 mmol) of potassium carbonate, followed by a solution of 623 mg (2.55 mmol) of 3(S)-hydroxybutyl p-toluenesulphonate in 5 ml of acetonitrile The mixture is stirred at 80° C. for 2 h, followed by addition of 20 ml of water and extraction twice with ethyl acetate. The organic phase is dried over sodium sulphate and then concentrated under reduced pressure. The solid obtained is chromatographed on a column of silica, with a 1/1 mixture of ethyl acetate and cyclohexane, then triturated in diisopropyl ether. 420 mg of product are obtained.
Melting point: 102° C.

EXAMPLE 6

[3(S),3a(S),7(R)]-(+)-3-Methoxymethyl-7-[4,4,4-trifluoro-3-hydroxybutoxy]-3,3a,4,5-tetrahydro-1H-oxazolo[3,4-a]quinolin-1-one 6.1. 1-Benzoyl-2-cyano-6-methoxy-1,2-dihydroquinoline A solution of 10 g (63 mmol) of 6-methoxyquinoline in 80 ml of dichloromethane is mixed with a solution of 12.4 g (188 mmol) of potassium cyanide, and 14.5 ml (125 mmol) of benzoyl chloride are then added slowly. The mixture is stirred for 18 h, the organic phase is then separated off and the aqueous phase is extracted with dichloromethane. The organic phases are washed with aqueous 5% hydrochloric acid solution and then with water, with aqueous sodium hydroxide solution and again with water, they are dried over sodium sulphate and the solvent is evaporated off under reduced pressure. The oil obtained is crystallized from 95% ethanol. 13.4 g of product are obtained.
Melting point: 124° C.

6.2. 2-Carboxy-6-methoxyquinoline 270 ml of 48% hydrobromic acid are added to a solution of 217 g (0,747 mol) of 1-benzoyl-2-cyano-6-methoxy-1,2-dihydroquinoline in 270 ml of acetic acid, and the mixture is heated at reflux for 30 min. It is filtered and rinsed with diethyl ether, and the solid obtained is then suspended in 2 l of water and heated to 90° C. Aqueous ammonia is then added until the pH=8–9 and the mixture is filtered while hot. The filtrate is acidified at 50° C., by adding acetic acid until the pH=4–5, and is then cooled. The crystallized product is filtered off, rinsed with water and then recrystallized from 250 ml of acetic acid and rinsed with diethyl ether. 129 g of product are obtained.
Melting point: 187° C.

6.3. 6-Methoxy-2-methoxycarbonylquinoline 230 ml (3.17 mol) of thionyl chloride are run dropwise onto a suspension of 129 g (0.635 mol) of 2-carboxy-6-methoxyquinoline in 1200 ml of toluene, and the mixture is heated for 3 h 30 min. After concentrating the solution under reduced pressure, the solid obtained is dissolved in 300 ml of methanol. The mixture is stirred for 30 min, the solvent is then evaporated off under reduced pressure, and the product obtained is taken up in diethyl ether and isolated by filtration. The solid obtained is taken up in ethyl acetate and dilute aqueous ammonia, and the organic phase is then separated out, treated with animal black, filtered and concentrated under reduced pressure. 90 g of product are thus obtained.
Melting point: 129° C.

6.4. (±)-6-Methoxy-2-methoxycarbonyl-1,2,3,4-tetrahydroquinoline

To a solution of 50 g (0.23 mol) of 6-methoxy-2-methoxycarbonylquinoline in 1000 ml of methanol is added 6N hydrochloric ethanol solution until the pH=1, followed by hydrogenation for 18 h in the presence of 2.6 g of hydrated platinum oxide. The catalyst is then removed by filtration and the solvent is evaporated off under reduced pressure. After triturating the product in a mixture of diisopropyl ether and petroleum ether, 56 g of product are obtained in the form of hydrochloride.
Melting point: 129° C.

After treatment with dilute aqueous ammonia, extraction with ethyl acetate, drying over sodium sulphate and evaporation of the solvent under reduced pressure, the base is recovered.
Melting point:<50° C.

6.5. Ethyl (±)-6-methoxy-2-methoxycarbonyl-1,2,3,4-tetrahydroquinoline-1-carboxylate To a solution of 69.3 g (0,313 mol) of (±)-6-methoxy-2-methoxycarbonyl-1,2,3,4-tetrahydroquinoline and 39 ml (0.407 mol) of ethyl chloroformate in 1400 ml of dichloromethane are added 85 g (0.63 mol) of potassium carbonate, and the mixture is heated at reflux for 18 h. The mixture is filtered, the filtrate is concentrated under reduced pressure and the residue is chromatographed on a column of silica, with a 3/7 mixture of ethyl acetate and cyclohexane. 80.4 g of product are obtained in the form of an oil.

6.6. Ethyl S-(−)-6-methoxy-2-methoxycarbonyl-1,2,3,4-tetrahydroquinoline-1-carboxylate and ethyl R-(+)-2-carboxy-6-methoxy-1,2,3,4-tetrahydroquinoline-1-carboxylate 3 g (10.2 mmol) of ethyl (±)-6-methoxy-2-methoxycarbonyl-1,2,3,4-tetrahydroquinoline-1-carboxylate are suspended in 80 ml of 0.01M phosphate buffer (potassium dihydrogen phosphate + disodium phosphate), at pH=7. The pH is then adjusted to 7.3 by addition of aqueous 1M sodium hydroxide solution, and 7.5 g of sheep liver acetone powder are added. The mixture is stirred for 14 h at room temperature, while keeping the pH constant by addition of aqueous 1M sodium hydroxide solution, the reaction mixture is then filtered on Celite and the Celite is rinsed with about 400 ml of diethyl ether. After extraction of the aqueous phase with 3 times 400 ml of diethyl ether, the organic phases are combined, dried over magnesium sulphate and filtered and the solvent is then evaporated off under vacuum. 1.5S g of an oily product corresponding to ethyl S-(−)-6-methoxy-2-methoxycarbonyl-1,2,3,4-tetrahydroquinoline-1-carboxylate are obtained.
ee: 99% by chiral HPLC
$[\alpha]_D^{20}=-54°7$ (c=0.9; dichloromethane)

The aqueous phase is acidified to pH=4.5 by addition of 10% hydrochloric acid and is then extracted with 3 times 100 ml of diethyl ether. The ether phases are combined, dried over magnesium sulphate and filtered, and the solvent is evaporated off under vacuum. 1.04 g of ethyl R-(+)-2-carboxy-6-methoxy-1,2,3,4-tetrahydroquinoline-1-carboxylate are obtained.

ee: 88% by chiral HPLC
$[\alpha]_D^{20}=+66°5$ (c=0.99; dichloromethane)

6.7. Ethyl S-(−)-2-formyl-6-methoxy-1,2,3,4-tetrahydroquinoline-1-carboxylate

To a solution of 34.6 g (0.118 mol) of ethyl S-(−)-6-methoxy-2-methoxycarbonyl-1,2,3,4-tetrahydroquinoline-1-carboxylate in 700 ml of toluene are added dropwise, at −70° C., 235 ml (0.234 mol) of a 1.5M solution of diisobutylaluminium hydride in toluene. The mixture is stirred for 15 min at −70° C., then 17 ml of methanol are run in slowly with stirring while allowing the mixture to return to rom temperature. 1.5 l of 1.5M hydrochloric acid solution are added, the organic phase is then separated out and the aqueous phase is extracted with diethyl ether. The organic phases are washed several times with water and the solvent is then evaporated off under reduced pressure. 23.8 g of product are obtained.
$[\alpha]_D^{20}=-43.1°$ (c=1; dichloromethane)

6.8. [3(S),3a(S)]-(+)- and [3(R), 3a(S)]-(+)-3-Ethenyl-7-methoxy-3,3a,4,5-tetrahydro-1H-oxazolo[3,4-a]quinolin-1-one A solution of 23.8 g (90 mmol) of ethyl S-(−)-2-formyl-6-methoxy-1,2,3,4-tetrahydroquinoline-1-carboxylate in 260 ml of tetrahydrofuran is cooled to −40° C. and 99 ml (99 mmol) of 1M vinylmagnesium bromide are added, under argon and with magnetic stirring, over 1 h 30. The mixture is then stirred for 1 h, followed by addition of chilled saturated aqueous ammonium chloride solution. The mixture is extracted twice with diethyl ether, washed with water and dried over sodium sulphate, and the solvent is evaporated off under reduced pressure. An oil is obtained, which is redissolved in 172 ml of toluene and heated to reflux in order to remove the traces of water. 0.8 ml of a 10% solution of sodium methoxide in methanol is added at 90° C. The mixture is again heated at reflux, with the ethanol formed being distilled off, and is then allowed to return to room temperature and the solution is chromatographed on a column of silica, with a 4/1 mixture of cyclohexane and ethyl acetate.

5.3 g of [3(S),3a(S)] compound, melting point: 80°–83° C.; $[\alpha]_D^{20}=+54.6°$ (c=1; dichloromethane) and 3 g of [3(R),3a (S)]compound are obtained, melting point: 137°–138° C.; $[\alpha]_D^{20}+41°8$ (c=1; dichloromethane).

6.9. [3(S),3a(S)]-(+)-3-Ethenyl-7-hydroxy-3,3a,4,5-tetrahydro-1H-oxazolo[3,4-a]quinolin-1-one To a solution of 5.3 g (22 mmol) of [3(S),3a(S)]-(+)-3-ethenyl-7-methoxy-3,3a,4,5-tetrahydro-1H-oxazolo[3,4-a]quinolin-1-one in 13 ml of dichloromethane are added dropwise, at 0° C., 43 ml (43 mmol) of a 1M solution of boron tribromide in dichloromethane. The mixture is stirred for 30 min, followed by addition of dilute aqueous ammonia to the point of neutrality. 5 to 10 ml of methanol are then added, and the reaction medium is concentrated by half under reduced pressure and filtered. The precipitate is rinsed with water and then with diethyl ether and dried. 4.7 g of product are obtained.
Melting point: 215° C.
$[\alpha]_D^{20}=+64.8°$ (c=1; dimethyl sulphoxide)

6.10. [3(S),3a(S),7(R)]-(+)-3-Ethenyl-7-[4,4,4-trifluoro-3-hydroxybutoxy]-3,3a,4,5-tetrahydro-1H-oxazolo[3,4-a]quinolin-1-one To a solution of 4.7 g (20 mmol) of [3(S),3a(S)]-(+)-3-ethenyl-7-hydroxy-3,3a,4,5-tetrahydro-1H-oxazolo[3,4-a]quinolin-1-one in 55 ml of acetonitrile are added 5.6 g (41 mmol) of potassium carbonate followed by 9.1 g (31 mmol) of 3(R)-hydroxy-4,4,4-trifluorobutyl p-toluenesulphonate. The mixture is heated at reflux for 16 h and is then diluted with dichloromethane and washed with water. The organic phase is then dried over sodium sulphate, followed by evaporation of the solvent under reduced pressure. The oil obtained is purified by chromatography on a column of silica. After crystallization from diisopropyl ether, 6.0 g of product are obtained.
Melting point: 145°–146° C.
$[\alpha]_D^{20}=+78.4°$ (c=1; methanol)

6.11. [3(S),3a(S),7(R)]-(+)-3-Ethenyl-7-[4,4,4-trifluoro-3-benzyloxybutoxy]-3,3a,4,5-tetrahydro-1H-oxazolo[3,4-a]quinolin-1-one To a solution of 6.0 g (17 mmol) of [3(S),3a(S),7(R)]-(+)-3-ethenyl-7-[4,4,4-trifluoro-3-hydroxybutoxy]-3,3a,4,5-tetrahydro-1H-oxazolo[3,4-a]quinolin-1-one in 60 ml of toluene are added a solution of 2.7 g (67 mmol) of sodium hydroxide in 2.7 ml of water, 0.53 g (1.7 mmol) of tetrabutylammonium bromide and then 6.0 ml (50 mmol) of benzyl bromide. The mixture is stirred at room temperature for 16 h and is then extracted with ethyl acetate, washed with water and dried over sodium sulphate, and the solvent is evaporated off under reduced pressure. The oil obtained is purified by chromatography on a column of silica, with an 8/2 mixture of cyclohexane and ethyl acetate. 7.1 g of product are obtained in the form of an oil which crystallizes slowly.
Melting point: 84° C.
$[\alpha]_D^{20}=+111°$ (c=1; dichloromethane)

6.12. [3(S),3a(S),7(R)]-(+)-3-Hydroxymethyl-7-[4,4,4-trifluoro-3-benzyloxybutoxy]-3,3a,4,5-tetrahydro-1H-oxazolo[3,4-a]quinolin-1-one Ozone is sparged, for 2 h at −40° C., into a solution of 7.0 g (16 mmol) of [3(S),3a(S),7(R)]-(+)-3-ethenyl-7-[4,4,4-trifluoro-3-benzyloxybutoxy]-3,3a,4,5-tetrahydro-1H-oxazolo[3,4-a]quinolin-1-one in 170 ml of dichloromethane and 240 ml of methanol. The ozone is then stripped off with a stream of nitrogen, followed by addition of 5.9 g (160 mmol) of sodium borohydride, at the same temperature. After 5 min, 5.7 ml (78 mmol) of dimethyl sulphide are added, and the mixture is left to return to room temperature and then washed with water, and the organic phase is dried over sodium sulphate and concentrated under reduced pressure. The product obtained is triturated with diethyl ether and then filtered. 4.7 g of product are obtained.
Melting point: 118° C.
$[\alpha]_D^{20}=+111.1°$ (c=1; dichloromethane)

6.13. [3(S),3a(S),7(R)]-(+)-3-Methoxymethyl-7-[4,4,4-trifluoro-3-benzyloxybutoxy]-3,3a,4,5-tetrahydro-1H-oxazolo[3,4-a]quinolin-1-one To a solution of 4.6 g (10 mmol) of [3(S),3a(S),7(R)]-(+)-3-hydroxymethyl-7-[4,4,4-trifluoro-3-benzyloxybutoxy]-3,3a,4,5-tetrahydro-1H-oxazolo[3,4-a]quinolin-1-one in 60 ml of toluene are added 0.32 g (1 mmol) of tetrabutylammonium bromide, followed by 7.7 g (61 mmol) of dimethyl sulphate and a solution of 3.2 g (82 mmol) of sodium hydroxide in 3.2 ml of water. The mixture is stirred for 1 h, diluted in ethyl acetate and the organic phase is then extracted, washed with water and dried over sodium sulphate, and the solvent is evaporated off under reduced pressure. By chromatography on a column of silica with a 7/3 mixture of cyclohexane and ethyl acetate, 6.2 g of product are obtained in the form of an oil.
$[\alpha]_D^{20}=+115.4°$ (c=1; dichloromethane).

6.14. [3(S),3a(S),7(R)]-(+)-3-Methoxymethyl-7-[4,4,4-trifluoro-3-hydroxybutoxy]-3,3a, 4,5-tetrahydro-1H-oxazolo[3,4-a]quinolin-1-one A solution of 4.1 g (8.8 mmol) of [3(S),3a(S),7(R)]-(+)-3-methoxymethyl-7-[4,4,4-trifluoro-3-benzyloxybutoxy]-3,3a,4,5-tetrahydro-1H-oxazolo[3,4-a]quinolin-1-one in 80 ml of ethanol is hydrogenated for 1 h, in the presence of 0.8 g of 10% palladium-on-charcoal containing 50% of water and traces of hydrochloric ethanol. The mixture is then filtered on silica and the solvent is evaporated off under reduced pressure. The product is crystallized from a mixture of acetone and diisopropyl ether and then from a 97/3 mixture of diisopropyl ether and isopropanol. 1.0 g of product is obtained.
Melting point: 120.7°–120.9° C.
[60 $]_D^{20}$=+105.4° (c=1; methanol)

EXAMPLE 7

[3(R),3a(S),7(R)]-(+)-3-Methoxymethyl-7-[4,4,4-trifluoro-3-hydroxybutoxy]-3,3a,4,5-tetrahydro-1H-oxazolo[3,4-a]quinolin-1-one 7.1. [3(R),3a(S)]-(+)-3-Ethenyl-7-hydroxy-3,3a,4,5-tetrahydro-1H-oxazolo[3,4-a]quinolin-1-one 2.0 g (8.0 mmol) of [3(R),3a(S)]-(+)-3-ethenyl-7-methoxy-3,3a,4,5-tetrahydro-1H-oxazolo[3,4-a]quinolin-1-one (obtained in Step 8 of Example 6) are treated under the conditions described in Step 9 of Example 6. 1.9 g of product are obtained.
$[\alpha]_D^{20}$=+47.2° (c=1; dimethyl sulphoxide).

7.2. [3(R),3a(S),7(R)]-(+)-3-Ethenyl-7-[4,4,4-trifluoro-3-hydroxybutoxy]-3,3a,4,5-tetrahydro-1H-oxazolo[3,4-a]quinolin-1-one A solution of 1.9 g (8.0 mmol) of [3(R),3a(S)]-(+)-3-ethenyl-7-hydroxy-3,3a,4,5-tetrahydro-1H-oxazolo[3,4-a]quinolin-1-one in 26 ml of acetonitrile and 10 ml of dimethylformamide is treated under the conditions described in Step 10 of Example 6.
2.6 g of product are obtained.
Melting point: 143°–145° C.
$[\alpha]_D^{20}$=+60.2° (c=1; methanol)

7.3. [3(R),3a(S),7(R)]-(+)-3-Ethenyl-7-[4,4,4,-trifluoro-3-benzyloxybutoxy]-3,3a,4,5-tetrahydro-1H-oxazolo[3,4-a]quinolin-1-one 2.5 g (7.0 mmol) of [3(R),3a(S),7(R)]-(+)-3-ethenyl-7-[4,4,4-trifluoro-3-hydroxybutoxy]-3,3a,4,5-tetrahydro-1H-oxazolo[3,4-a]quinolin-1-one are treated under the conditions described in Step 11 of Example 6.
3.0 g of product are obtained.
Melting point: 73°–74° C.
$[\alpha]_D^{20}$=+102.7° C. (c=1; dichloromethane)

7.4. [3(R),3a(S),7(R)]-(+)-3-Hydroxymethyl-7-[4,4,4-trifluoro-3-benzyloxybutoxy]-3,3a,4,5-tetrahydro-1H-oxazolo[3,4-a]quinolin-1-one 3.0 g (6.7 mmol) of [3(R),3a(S),7(R)]-(+)-3-ethenyl-7-[4,4,4-trifluoro-3-benzyloxybutoxy]-3,3a,4,5-tetrahydro-1H-oxazolo[3,4-a]quinolin-1-one are treated under the conditions described in Step 12 of Example 6.
2.1 g of product are obtained.
Melting point: 107° C.
$[\alpha]_D^{20}$=+63.8° (c=1; dichloromethane).

7.5. [3(R),3a(S),7(R)]-(+)-3-Methoxymethyl-7-[4,4,4-trifluoro-3-benzyloxybutoxy]-3,3a,4,5-tetrahydro-1H-oxazolo[3,4-a]quinolin-1-one A solution of 2.1 g (4.7 mmol) of [3(R),3a(S),7(R)]-(+)-3-hydroxymethyl-7-[4,4,4-trifluoro-3-benzyloxybutoxy]-3,3a,4,5-tetrahydro-1H-oxazolo[3,4-a]quinolin-1-one in 30 ml of toluene and 3 ml of dichloromethane is treated under the conditions described in Step 13 of Example 6. 1.8 g of product are obtained in the form of an oil.
$[\alpha]_D^{20}$=+64.8° (c=1; dichloromethane)

7.6. [3(R),3a(S),7(R)]-(+)-3-Methoxymethyl-7-[4,4,4-trifluoro-3-hydroxybutoxy]-3,3a, 4,5-tetrahydro-1H-oxazolo[3,4-a]quinolin-1-one 1.8 g (3.9 mmol) of [3(R),3a(S),7(R)]-(+)-3-methoxymethyl-7-[4,4,4-trifluoro-3-benzyloxybutoxy]-3,3a,4,5-tetrahydro-1H-oxazolo[3,4-a]quinolin-1-one are treated under the conditions described in Step 14 of Example 6.
0.9 g of product is obtained.
Melting point: 165.3°–165.5° C.
$[\alpha]_D^{20}$=+16.7° (c=1; methanol)

EXAMPLE 8

[3(R),3a(R),7(R)]-(–)-3-Methoxymethyl-7-[4,4,4-trifluoro-3-hydroxybutoxy]-3,3a, 4,5-tetrahydro-1H-oxazolo [3,4-a]quinolin-1-one 8.1. Ethyl R-(+)-6-methoxy-2-methoxycarbonyl-1,2,3,4-tetrahydroquinoline-1-carboxylate 21.8 ml (302 mmol) of thionyl chloride are run dropwise, at –40° C., into 170 ml of methanol. After 10 min, 16.9 g (60.4 mmol) of ethyl R-(+)-2-carboxy-6-methoxy-1,2,3,4-tetrahydroquinoline-1-carboxylate (obtained in Step 6 of Example 6) are added, the mixture is stirred for 3 h while allowing the temperature to rise from –40° to 0° C., and it is then poured into a mixture of ice and water and aqueous ammonia is added to the point of neutrality. The mixture is extracted with ethyl acetate, the organic phase is washed with water and dried over sodium sulphate, and the solvent is evaporated off. 18 g of product are obtained in the form of an oil.
$[\alpha]_D^{20}$=+52° (c=1; dichloromethane)

8.2. Ethyl R-(+)-2-formyl-6-methoxy-1,2,3,4-tetrahydroquinoline-1-carboxylate 18 g (0.061 mol) of ethyl R-(+)-6-methoxy-2-methoxycarbonyl-1,2,3,4-tetrahydroquinoline-1-carboxylate are treated under the conditions described in Step 7 of Example 6. 11.6 g of product are obtained.
$[\alpha]_D^{20}$=+67.9° (c=1; dichloromethane).

8.3. [3(R),3a(R)]-(–)- and [3(S),3a(R)]-(–)-3-Ethenyl-7-methoxy-3,3a,4,5-tetrahydro-1H-oxazolo[3,4-a]quinolin-1-one 11.5 g (43.6 mmol) of ethyl. R-(+)-2-formyl-6-methoxy-1,2,3,4-tetrahydroquinoline-1-carboxylate are treated under the conditions described in Step 8 of Example 6.
4.0 g of [3(R),3a(R)]compound,
melting point: 80° C.;
$[\alpha]_D^{20}$=–48.8° (c=1; dichloromethane) and 2.2 g of compound [3(S),3a(R)] compound are obtained, melting point: 140° C.;
$[\alpha]_D^{20}$=–39° (c=1, dichloromethane)

8.4. [3(R),3a(R)]-(–)-3-Ethenyl-7-hydroxy-3,3a,4,5-tetrahydro-1H-oxazolo[3,4-a]quinolin-1-one 4.0 g (16 mmol) of [3(R),3a(R)]-(–)-3-ethenyl-7-methoxy-3,3a,4,5-tetrahydro-1H-oxazolo[3,4-a]quinolin-1-one are treated under the conditions described in Step 9 of Example 6. 2.5 g of product are obtained.
$[\alpha]_D^{20}$=–45.2° (c=1; dimethyl sulphoxide).

8.5. [3(R),3a(R),7(R)]-(–)-3-Ethenyl-7-[4,4,4-trifluoro-3-hydroxybutoxy]-3,3a,4,5-tetrahydro-1H-oxazolo[3,4-a]quinolin-1-one A solution of 2.35 g (10 mmol) of [3(R),3a(R)]-(–)-3-ethenyl-7-hydroxy-3,3a,4,5-tetrahydro-1H-oxazolo[3,4-a]quinolin-1-one in 25 ml of acetonitrile and 10 ml of dimethylformamide is treated under the conditions described in Step 10 of Example 6.
2.5 g of product are obtained.
Melting point: 92° C.
$[\alpha]_D^{20}$=–31.4° (c=1; dichloromethane).

8.6. [3(R),3a(R),7(R)]-(+)-3-Ethenyl-7-[4,4,4-trifluoro-3-benzyloxybutoxy]-3,3a,4,5-tetrahydro-1H-oxazolo[3,4-a]quinolin-1-one 1.82 g (5.09 mmol) of [3(R),3a(R),7(R)]-(−)-3-ethenyl-7-[4,4,4-trifluoro-3-hydroxybutoxy]-3,3a,4,5-tetrahydro-1H-oxazolo[3,4-a]quinolin-1-one are treated under the conditions described in Step 11 of Example 6.

2.1 g of product are obtained in the form of an oil.

$[\alpha]_D^{20}$=+28.9° (c=1; dichloromethane).

8.7. [3(R),3a(R),7(R)]-(+)-3-Hydroxymethyl-7-[4,4,4-trifluoro-3-benzyloxybutoxy]-3,3a,4,5-tetrahydro-1H-oxazolo[3,4-a]quinolin-1-one 2.1 g (4.7 mmol) of [3(R),3a(R),7(R)]-(+)-3-ethenyl-7-[4,4,4-trifluoro-3-benzyloxybutoxy]-3,3a,4,5-tetrahydro-1H-oxazolo[3,4-a]quinolin-1-one are treated under the conditions described in Step 12 of Example 6. 1.4 g of product are obtained.

Melting point: 110° C.

$[\alpha]_D^{20}$=+15.5° (c=1; dichloromethane)

8.8. [3(R),3a(R),7(R)]-(+)-3-Methoxymethyl-7-[4,4,4-trifluoro-3-benzyloxybutoxy]-3,3a,4,5-tetrahydro-1H-oxazolo[3,4-a]quinolin-1-one 1.4 g (3.1 mmol) of [3(R),3a(R),7(R)]-(+)-3-hydroxymethyl-7-[4,4,4-trifluoro-3-benzyloxybutoxy]-3,3a,4,5-tetrahydro-1H-oxazolo[3,4-a]quinolin-1-one are treated under the conditions described in Step 13 of Example 6. 1.0 g of product is obtained in the form of an oil.

$[\alpha]_D^{20}$=+15.8° (c=1; dichloromethane)

8.9. [3(R),3a(R),7(R)]-(−)-3-Methoxymethyl-7-[4,4,4-trifluoro-3-hydroxybutoxy]-3,3a, 4,5-tetrahydro-1H-oxazolo[3,4-a]quinolin-1-one 1.0 g (2.2 mmol) of [3(R),3a(R),7(R)]-(+)-3-methoxymethyl-7-[4,4,4-trifluoro-3-benzyloxybutoxy]-3,3a,4,5-tetrahydro-1H-oxazolo[3,4-a]quinolin-1-one is treated under the conditions described in Step 14 of Example 6. After evaporation of the solvent under reduced pressure and chromatography on a column of silica, with a 1/1 mixture of cyclohexane and ethyl acetate, 0.65 g of product is obtained.

Melting point: 90° C.

$[\alpha]_D^{20}$=−35.6° (c=1; methanol)

EXAMPLE 9

[3(S),3a(R),7(R)]-(+)-3-Methoxymethyl-7-[4,4,4-trifluoro-3-hydroxybutoxy]-3,3a,4,5-tetrahydro-1H-oxazolo[3,4-a]quinolin-1-one 9.1. [3(S),3a(R)]-(−)-3-Ethenyl-7-hydroxy-3,3a,4,5-tetrahydro-1H-oxazolo[3,4-a]quinolin-1-one 2.2 g (9.0 mmol) of [3(S),3a(R)]-(−)-3-ethenyl-7-methoxy-3,3a,4,5-tetrahydro-1H-oxazolo[3,4-a]quinolin-1-one (obtained in Step 3 of Example 8) are treated under the conditions described in Step 9 of Example 6. 1.8 g of product are obtained.

$[\alpha]_D^{20}$=−50.9° (c=1; dimethyl sulphoxide)

9.2. [3(S),3a(R),7(R)]-(−)-3-Ethenyl-7-[4,4,4-trifluoro-3-hydroxybutoxy]-3,3a,4,5-tetrahydro-1H-oxazolo[3,4-a]quinolin-1-one 1.7 g (7.5 mmol) of [3(S),3a(R)]-(−)-3-ethenyl-7-hydroxy-3,3a,4,5-tetrahydro-1H-oxazolo[3,4-a]quinolin-1-one are treated under the conditions described in Step 10 of Example 6. After crystallization from diethyl ether, 1.8 g of product are obtained.

Melting point: 145° C.

$[\alpha]_{D20}$=−16.4° (c=1, methanol)

9.3. [3(S),3a(R),7(R)]-(+)-3-Ethenyl-7-[4,4,4-trifluoro-3-benzyloxybutoxy]-3,3 a,4,5-tetrahydro-1H-oxazolo [3,4-a]quinolin-1-one 1.77 g (4.95 mmol) of [3(S),3a(R),7(R)]-(−)-3-ethenyl-7-[4,4,4-trifluoro- 3-hydroxybutoxy]-3,3a,4,5-tetrahydro-1H-oxazolo[3,4-a]quinolin-1-one are treated under the conditions described in Step 11 of Example 6. After purification by chromatography on a column of silica, with a 1/9 mixture of cyclohexane and chloroform, 2.0 g of product are obtained.

$[\alpha]_D^{20}$=+42.7° (c=1; dichloromethane)

9.4. [3(S),3a(R),7(R)]-(+)-3-Hydroxymethyl-7-[4,4,4-trifluoro-3-benzyloxybutoxy]-3,3a,4,5-tetrahydro-1H-oxazolo[3,4-a]quinolin-1-one 1.9 g (4.2 mmol) of [3(S),3a(R),7(R)]-(+)-3-ethenyl-7-[4,4,4-trifluoro-3-benzyloxybutoxy]-3,3a,4,5-tetrahydro-1H-oxazolo[3,4-a]quinolin-1-one are treated under the conditions described in Step 12 of Example 6. After concentrating the organic phase under reduced pressure, 1.7 g of product are obtained.

Melting point: 98° C.

$[\alpha]_{D20}$=+69.5° (c=1; dichloromethane)

9.5. [3(S),3a(R),7(R)]-(+)-3-Methoxymethyl-7-[4,4,4-trifluoro-3-benzyloxybutoxy]-3,3a,4,5-tetrahydro-1H-oxazolo[3,4-a]quinolin-1-one 1.68 g (3.72 mmol) of [3(S),3a(R),7(R)]-(+)-3-hydroxymethyl-7-[4,4,4-trifluoro-3-benzyloxybutoxy]-3,3a, 4,5-tetrahydro-1H-oxazolo[3,4-a]quinolin-1-one are treated under the conditions described in Step 13 of Example 6. By chromatography on a column of silica, with a 6/4 mixture of cyclohexane and ethyl acetate, 1.35 g of product are obtained in the form of an oil.

$[\alpha]_D^{20}$=+61.6° (c=1; dichloromethane)

9.6. [3(S),3a(R),7(R)]-(+)-3-Methoxymethyl-7-[4,4,4-trifluoro-3-hydroxybutoxy]-3,3a,4,S-tetrahydro-1H-oxazolo[3,4-a]quinolin-1-one 1.29 g (2.77 mmol) of 3(S),3a(R),7(R)]-(+)-3-methoxymethyl-7-[4,4,4-trifluoro-3-benzyloxybutoxy]-3, 3a,4,5-tetrahydro-1H-oxazolo[3,4-a]quinolin-1-one are treated under the conditions described in Step 14 of Example 6. 0.33 g of compound is obtained.

Melting point: 103.6°–103.8° C.

$[\alpha]_D^{20}$=+49.1° (c=1; methanol)

EXAMPLE 10

7(R)-(4,4,4-Trifluoro-3-hydroxybutoxy)-3,3a,4,5-tetrahydro-1H-oxazolo[3,4-a]quinolin-1-one 10.1. 7-Methoxy-3,3a,4,5-tetrahydro-1H-oxazolo[3,4-a] quinolin-1-one To a solution of 10.9 g (41.4 mmol) of ethyl 2-formyl-6-methoxy-1,2,3,4-tetrahydroquinoline-1-carboxylate in 100 ml of methanol, cooled to 0° C., are added portionwise 2.2 g (41.4 mmol) of potassium borohydride. The medium is stirred for 1 h and then hydrolyzed, diluted with water and extracted with diethyl ether. The organic phase is then washed with water and dried over sodium sulphate, and the solvent is evaporated off under reduced pressure. The oil obtained is redissolved in 90 ml of toluene, the solution is heated to reflux in order to remove traces of water, and a catalytic amount of 10% sodium methoxide in methanol is then added at 90° C. The mixture is again heated to reflux in order to remove the ethanol formed, followed by evaporation of the solvent. The residue is taken up in ethyl acetate and washed with water, then the organic phase is dried over sodium sulphate and concentrated under reduced pressure. After chromatography on a column of silica with a 4/1 mixture of heptane and ethyl acetate, 5.0 g of product are obtained.

Melting point: 99° C.

10.2. 7-Hydroxy-3,3a,4,5-tetrahydro-1H-oxazolo[3,4-a] quinolin-1-one

To a solution of 4.6 g (21 mmol) of 7-methoxy-3,3a,4,5-tetrahydro-1H-oxazolo[3,4-a]quinolin-1-one in 50 ml of dichloromethane are added dropwise, at 0° C., 4.0 ml (42 mmol) of boron tribromide. After one hour, the medium is hydrolyzed by addition of aqueous ammonia to the point of neutrality. The precipitate formed is then filtered off and dried under vacuum.
3.1 g of product are obtained.
Melting point:>260° C.

10.3. 7(R)-(4,4,4-Trifluoro-3-hydroxybutoxy)-3,3a,4,5-tetrahydro-1H-oxazolo[3,4-a]quinolin-1-one To a solution of 2.0 g (9.7 mmol) of 7-hydroxy-3,3a,4,5-tetrahydro-1H-oxazolo[3,4-a]quinolin-1-one in 10 ml of acetonitrile and 10 ml of dimethylformamide are added 4.3 g (15 mmol) of 3(R)-hydroxy-4,4,4-trifluorobutyl tosylate and 4.0 g (29 mmol) of potassium carbonate. The mixture is stirred for 4 h at 90° C. and then diluted with ethyl acetate and washed with water. The organic phase is dried over sodium sulphate and the solvent is then evaporated off under reduced pressure. After purification of the oil obtained by chromatography on a column of silica, with a 4/1 mixture of heptane and ethyl acetate, 1.9 g of product are obtained.
Melting point: 188° C.

EXAMPLE 11

S-(+)-7-(4,4,4-trifluorobutoxy)-3,3a,4,5-tetrahydro-1H-oxazolo[3,4-a]quinolin-1-one 11.1. S-(+)-7-Methoxy-3,3a,4,5-tetrahydro-1H-oxazolo[3,4-a]quinolin-1-one To a solution of 8.0 g (27 mmol) of ethyl S-(−)-6-methoxy-2-methoxycarbonyl-1,2,3,4-tetrahydroquinoline-1-carboxylate (obtained in Step 6 of Example 6) in 80 ml of diglyme is added portionwise 0.90 g (41 mmol) of lithium borohydride. The mixture is stirred for 3 hours at 50° C. and then poured into water and the product is extracted with ethyl acetate. The organic phase is dried over sodium sulphate and concentrated under reduced pressure, and the residue is triturated in petroleum ether containing a little isopropyl alcohol. 4.4 g of product are obtained.
Melting point: 112° C.
$[\alpha]_D^{20}$=+63.7° (c=1; dichloromethane)

According to the same process, starting with ethyl R-(+)-6-methoxy-2-methoxycarbonyl-1,2,3,4-tetrahydroquinoline-1-carboxylate, R-(−)-7-methoxy-3,3a,4,5-tetrahydro-1H-oxazolo[3,4-a]quinolin-1-one was obtained.
Melting point: 110° C.
$[\alpha]_D^{20}$=−40.1° (c=1; dichloromethane).

11.2. S-(+)-7-Hydroxy-3,3a,4,5-tetrahydro-1H-oxazolo[3,4-a]quinolin-1-one

To a solution of 4.3 g (20 mmol of S-(+)-7-methoxy-3,3a,4,5-tetrahydro-1H-oxazolo[3,4-a]quinolin-1-one in 40 ml of dichloromethane, cooled to 0° C., are added dropwise, at 0° C., 39 ml (39 mmol) of a 1M solution of boron tribromide in dichloromethane. The mixture is stirred for 1 hour while allowing the temperature to rise, then aqueous ammonia solution is added to the point of neutrality, and the precipitate formed is filtered off and dried. 3.0 g of product are obtained.
Melting point: >250° C.
$[\alpha]_D^{20}$=+51.4° (c=1; dimethyl sulphoxide).

According to the same process, starting with R-(−)-7-methoxy-3,3a,4,5-tetrahydro-1H-oxazolo[3,4-a]quinolin-1-one, R-(−)-7-hydroxy-3,3a,4,5-tetrahydro-1H-oxazolo[3,4-a]quinolin-1-one was obtained.
Melting point: >250° C.
$[\alpha]_D^{20}$=−46° (c=1; dimethyl sulphoxide)

11.3. S-(+)-7-(4,4,4-Trifluorobutoxy)-3,3a,4,5-tetrahydro-1H-oxazolo[3,4-a]quinolin-1-one To a solution of 1.9 g (9.3 mmol) of S-(+)-7-hydroxy-3,3a,4,5-tetrahydro-1H-oxazolo[3,4-a]quinolin-1-one in a mixture of 10 ml of dimethylformamide and 40 ml of acetonitrile are added 2.7 g (13 mmol) of 1-bromo-4,4,4-trifluorobutane and 2.6 g (18 mmol) of potassium carbonate. The mixture is heated for 3 hours at 90° C. and is then diluted with ethyl acetate and washed with water. The organic phase is then dried over sodium sulphate and concentrated under reduced pressure, and the residue is chromatographed on a column of silica, with dichloromethane containing 0.5% of methanol. After recrystallization from isopropyl alcohol, 2.1 g of product are obtained.
Melting point: 121.3°–121.4° C.
$[\alpha]_D^{20}$=+33.8° (c=1; dichloromethane).

EXAMPLE 12 cis-(±)-3-Phenyl-7-(4,4,4-trifluorobutoxy)-3,3a,4,5-tetrahydro-1H-oxazolo[3,4-a]quinolin-1-one 12.1. cis- and trans-(±)-7-Methoxy-3-phenyl-3,3a,4,5-tetrahydro-1H-oxazolo[3,4-a]quinolin-1-one Starting with a solution of ethyl 2-formyl-6-methoxy-1,2,3,4-tetrahydroquinoline-1-carboxylate in methanol, cooled to 0° C., and phenylmagnesium bromide, these reactants being treated under conditions similar to those of Step 1 of Example 1, the cis derivative,
melting point: 99° C., and
the trans derivative,
melting point: 126° C., are obtained.

12.2. cis-(±)-7-Hydroxy-3-phenyl-3,3a,4,5-tetrahydro-1H-oxazolo[3,4-a]quinolin-1-one Starting with cis-(±)-7-methoxy-3-phenyl-3,3a,4,5-tetrahydro-1H-oxazolo[3,4-a]quinolin-1-one, which is treated under the conditions of Step 2 of Example 1, cis-(±)-7-hydroxy-3-phenyl-3,3a,4,5-tetrahydro-1H-oxazolo[3,4-a]quinolin-1-one is obtained.
Melting point: 242° C.

Starting with trans-(±)-7-methoxy-3-phenyl-3,3a,4,5-tetrahydro-1H-oxazolo[3,4-a]quinolin-1-one, trans-(±)-7-hydroxy-3-phenyl-3,3a,4,5-tetrahydro-1H-oxazolo[3,4-a]quinolin-1-one is obtained.
Melting point: 216° C.

12.3. cis-(±)-3-Phenyl-7-(4,4,4-trifluorobutoxy)-3,3a,4,5-tetrahydro-1H-oxazolo[3,4-a]quinolin-1-one To a solution of 0.65 g (2.3 mmol) of cis-(±)-7-hydroxy-3-phenyl-3,3a,4,5-tetrahydro-1H-oxazolo[3,4-a]quinolin-1-one in 15 ml of dimethylformamide are added 0.66 g (3.5 mmol) of 1-bromo-4,4,4-trifluorobutane and 0.64 g (4.6 mmol) of potassium carbonate. The mixture is heated for 4 hours at 90° C. and is then diluted with ethyl acetate and washed with water. The organic phase is then dried over sodium sulphate and concentrated under reduced pressure, and the residue is chromatographed on a column of silica, with cyclohexane containing 20% of ethyl acetate. After trituration in diisopropyl ether, 0.60 g of product is obtained.
Melting point: 129.5° C.

EXAMPLE 13 cis-(±)-3-Methyl-7-(4,4,4-trifluorobutoxy)-3,3a,4,5-tetrahydro-1H-oxazolo[3,4-a]quinolin-1-one 13.1. cis-(±)-7-Methoxy-3-methyl-3,3a,4,5-tetrahydro-1H-oxazolo[3,4-a]quinolin-1-one Starting with a solution of ethyl 2-formyl-6-methoxy-1, 2,3,4-tetrahydroquinoline-1-carboxylate in diethyl ether, cooled to 0° C., and methylmagnesium bromide, these reactants being treated under similar conditions to those of Step 1 of Example 1, the cis derivative,
melting point: 138°–139° C., and
the trans derivative,
melting point: 122°–123° C., are obtained. 13.2. cis-(±)-7-Hydroxy-3-methyl-3,3a,4,5-tetrahydro-1H-oxazolo[3,4-a]quinolin-1-one Starting with cis-(±)-7-methoxy-3-methyl-3,3a,4,5-tetrahydro-1H-oxazolo[3,4-a]quinolin-1-one, treated under the conditions of Step 2 of Example 1, cis-(±)-7-hydroxy-3-methyl-3,3a,4,5-tetrahydro-1H-oxazolo[3,4-a]quinolin-1-one is obtained.
Melting point: 258°–259° C.

Starting with trans-(±)-7-methoxy-3-methyl-3,3a,4,5-tetrahydro-1H-oxazolo[3,4-a]quinolin-1-one, trans-(±)-7-hydroxy-3-methyl-3,3a,4,5-tetrahydro-1H-oxazolo[3,4-a]quinolin-1-one is obtained.
Melting point: 240°–241° C.
13.3. cis-(±)-3-Methyl-7-(4,4,4-trifluorobutoxy)-3,3a,4,5-tetrahydro-1H-oxazolo[3,4-a]quinolin-1-one To a solution of 0.70 g (3.2 mmol) of cis-(±)-7-hydroxy-3-methyl-3,3a,4,5-tetrahydro-1H-oxazolo[3,4-a]quinolin-1-one in 15 ml of dimethylformamide are added 0.90 g (4.8 mmol) of 1-bromo-4,4,4-trifluorobutane and 0.90 g (6.4 mmol) of potassium carbonate. The mixture is heated at 90° C. for 4 hours and then diluted with ethyl acetate and washed with water. The organic phase is then dried over sodium sulphate and concentrated under reduced pressure, and the residue is chromatographed on a column of silica, with cyclohexane containing 20% of ethyl acetate. After trituration in diisopropyl ether, 0.80 g of product is obtained.
Melting point: 79.1°–79.2° C.

EXAMPLE 14

[3α,3aβ,7(R)]-3-ethyl-7-(4,4,4-trifluoro-3-hydroxybutoxy)-3,3a,4,5-tetrahydro-1H-oxazolo[3,4-a]quinolin-1-one 0.86 g (2.4 mmol) of [3α,3aβ,7(R)]-3-ethenyl-7-[4,4,4-trifluoro-3-hydroxybutoxy]-3,3a,4,5-tetrahydro-1H-oxazolo[3,4-a]quinolin-1-one (obtained in Example 1) are hydrogenated for 3 h in 20 ml of methanol, in the presence of 0.2 g of 5% palladium-on-charcoal containing 50% of water. The mixture is then filtered and concentrated to dryness under reduced pressure. After purification of the oil obtained by chromatography on a column of silica, with a 95/5 mixture of dichloromethane and methanol, and crystallization from diisopropyl ether, 0.47 g of product is obtained.
Melting point: 120°–131° C.

EXAMPLE 15

[3(S),3a(S),7(S)]-3-methoxymethyl-7-(4,4,4-trifluoro-3-hydroxybutoxy)-3,3a,4,5-tetrahydro-1H-oxazolo[3,4-a]quinolin-1-one 15.1. [3(S),3a(S)]-(+)-7-Benzyloxy-3-ethenyl-3,3a,4,5-tetrahydro-1H-oxazolo[3,4-a]quinolin-1-one Starting with [3(S),3a(S)]-(+)-3-ethenyl-7-hydroxy-3,3a,4,5-tetrahydro-1H-oxazolo[3,4-a]quinolin-1-one (obtained in Step 9 of Example 6), which is treated under the conditions described in Step 1 of Example 5, [3(S),3a(S)]-(+)-7-benzyloxy-3-ethenyl-3,3a,4,5-tetrahydro-1H-oxazolo[3,4-a]quinolin-1-one is obtained.

Melting point: 86°–90° C.
$[\alpha]_D^{20}$=+71.1° (c=1; dichloromethane).

According to the same process, the following compounds were obtained:

[3(S),3a(R)]-(−)-7-Benzyloxy-3-ethenyl-3,3a,4,5-tetrahydro-1H-oxazolo[3,4-a]quinolin-1-one
Melting point: 102° C.
$[\alpha]_D^{20}$=−45.2°.

[3(R),3a(S)]-(+)-7-Benzyloxy-3-ethenyl-3,3a,4,5-tetrahydro-1H-oxazolo[3,4-a]quinolin-1-one
Melting point: 98° C.
$[\alpha]_D^{20}$=+45.7°.

[3(R),3a(R)]-(−)-7-Benzyloxy-3-ethenyl-3,3a,4,5-tetrahydro-1H-oxazolo [3,4-a]quinolin-1-one
Melting point: 84° C.
$[\alpha]_D^{20}$=−62.1°.

15.2. [3(S),3a(S)]-(+)-7-Benzyloxy-3-hydroxymethyl-3,3a,4,5-tetrahydro-1H-oxazolo [3,4-a]quinolin-1-one Starting with the compound obtained in the above step, which is treated under conditions described in Step 2 of Example 5, [3(S),3a(S)]-(+)-7-benzyloxy-3-hydroxymethyl-3,3a,4,5-tetrahydro-1H-oxazolo[3,4-a]quinolin-1-one is obtained.
Melting point: 120°–40° C.
$[\alpha]_D^{20}$=+73.8° (c=1; dimethyl sulphoxide)

According to the same process, the following compounds were obtained:

[3(S),3a(R)]-(−)-7-Benzyloxy-3-hydroxymethyl-3,3a,4,5-tetrahydro-1H-oxazolo[3,4-a]quinolin-1-one in the form of a gum.
$[\alpha]_D^{20}$=−4.2°.

[3(R),3a(S)]-(+)-7-Benzyloxy-3-hydroxymethyl-3,3a,4,5-tetrahydro-1H-oxazolo[3,4-a]quinolin-1-one
Melting point: 138°–140° C.
$[\alpha]_D^{20}$=+4.8°.

[3(R),3a(R)]-(−)-7-Benzyloxy-3-hydroxymethyl-3,3a,4,5-tetrahydro-1H-oxazolo[3,4-a]quinolin-1-one in the form of a gum.
$[\alpha]_D^{20}$=−54.6°.

15.3. [3(S),3a(S)]-(+)-7-Benzyloxy-3-methoxymethyl-3,3a,4,5-tetrahydro-1H-oxazolo[3,4-a]quinolin-1-one To a solution of 1.7 g (0.052 mol) of [3(S),3a(S)]-(+)-7-benzyloxy-3-hydroxymethyl-3,3a,4,5-tetrahydro-1H-oxazolo[3,4-a]quinolin-1-one in 100 ml of toluene and 100 ml of dichloromethane are added 0.17 g (0.005 mol) of tetramethylammonium bromide and then 3.0 ml of dimethyl sulphate, followed by a solution of 1.7 g (0.041 mol) of sodium hydroxide in 1.7 ml of water. The mixture is stirred for 1 h 30 min and is then diluted with ethyl acetate. The organic phase is then separated off, washed with water and dried over sodium sulphate, and the solvent is evaporated off under reduced pressure. After chromatography on a column of silica, with a 3/2 mixture of cyclohexane and ethyl acetate, 1.2 g of product are obtained.
Melting point: 118°–120° C.
$[\alpha]_D^{20}$=+76.7° (c=1; dichloromethane)

According to the same process, the following compounds were obtained:

[3(S),3a(R)]-(−)-7-Benzyloxy-3-methoxymethyl-3,3a,4,5-tetrahydro-1H-oxazolo[3,4-a]quinolin-1-one
Melting point: 99° C.
$[\alpha]_D^{20}$=−2.2°.

[3(R),3a(S)]-(+)-7-Benzyloxy-3-methoxymethyl-3,3a,4,5-tetrahydro-1H-oxazolo [3,4-a]quinolin-1-one
Melting point: 96°–98° C.
$[\alpha]_D^{20}$=+1.1°.

[3(R),3a(R)]-(−)-7-Benzyloxy-3-methoxymethyl-3,3a,4,5-tetrahydro-1H-oxazolo [3,4-a]quinolin-1-one Melting point: 122° C.
$[\alpha]_D^{20}=-74°$.

15.4. [3(S),3a(S)]-(+)-7-Hydroxy-3-methoxymethyl-3,3a,4,5-tetrahydro-1H-oxazolo[3,4-a]quinolin-1-one A solution of 1.2 g (0.0035 mol) of [3(S),3a(S)]-(+)-7-benzyloxy-3-methoxymethyl-3,3a,4,5-tetrahydro-1H-oxazolo[3,4-a]quinolin-1-one is hydrogenated for 5 h under pressure and at ambient temperature in 50 ml of methanol and 40 ml of tetrahydrofuran, in the presence of 0.25 g of 10% palladium-on-charcoal containing 50% of water. The mixture is then filtered on silica and the solvent is evaporated off under reduced pressure. 0.9 g of product is obtained.

Melting point: 172°–176° C.
$[\alpha]_D^{20}=+99°$ (c=1; dimethyl sulphoxide)

According to the same process, the following compounds were obtained:

[3(S),3a(R)]-(+)-7-Hydroxy-3-methoxymethyl-3,3a,4,5-tetrahydro-1H-oxazolo[3,4-a]quinolin-1-one Melting point: 170° C.
$[\alpha]_D^{20}=+11.1°$.

[3(R),3a(S)]-(−)-7-Hydroxy-3-methoxymethyl-3,3a,4,5-tetrahydro-1H-oxazolo[3,4-a]quinolin-1-one Melting point: 166° C.
$[\alpha]_D^{20}=-8.2°$.

[3(R),3a(R)]-(−)-7-Hydroxy-3-methoxymethyl-3,3a,4,5-tetrahydro-1H-oxazolo[3,4-a]quinolin-1-one Melting point: 180° C.
$[\alpha]_D^{20}=-93.3°$.

15.5. [3(S),3a(S),7(S)]-(+)-3-Methoxymethyl-7-[4,4,4-trifluoro-3-hydroxybutoxy]-3,3a,4,5-tetrahydro-1H-oxazolo [3,4-a]quinolin-1-one Starting with 0.86 g (3.45 mmol) of [3(S),3a(S)]-(+)-7-hydroxy-3-methoxymethyl-3,3a,4,5-tetrahydro-1H-oxazolo [3,4-a]quinolin-1-one and 1.54 g (5.18 mmol) of 4,4,4-trifluoro-3(S)-hydroxybutyl p-toluenesulphonate, these reactants being treated under the conditions of Step 4 of Example 5, 0.38 g of product is obtained in the form of an oil.

$[\alpha]_D^{20}=+33.2°$ (c=1; methanol)

The compounds according to the invention are presented together in the following Table with their physical characteristics.

TABLE

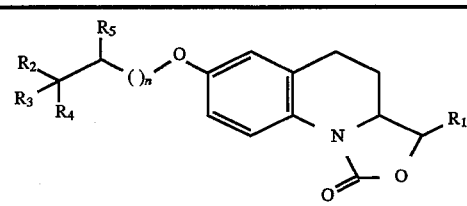

| No. | $R_1$ | $R_2(R_3)C(R_4)-CH(R_5)-(CH_2)_n-$ | Config. | m.p. (°C.) | $[\alpha]_D^{20}$ |
|---|---|---|---|---|---|
| 1 | −CH=CH$_2$ | OH | 3α, 3aα, 7(R) | 131.7 | |
| 2 | | | 3α, 3aβ, 7(R) | 135.8 | +78.4° |
| 3 | | | 3(S), 3a(S), 7(R) | 145–146 | +60.2° |
| 4 | | F$_3$C | 3(R), 3a(S), 7(R) | 143–145 | −31.4° |
| 5 | | | 3(R), 3a(R), 7(R) | 92 | −16.4° |
| 6 | | | 3(S), 3a(R), 7(R) | 145 | |
| 7 | −CH$_2$OH | OBn | 3α, 3aα, 7(R) | 101.7 | |
| 8 | | | 3α, 3aβ, 7(R) | 111.6 | +111.1° |
| 9 | | | 3(S), 3a(S), 7(R) | 118 | +63.8° |
| 10 | | F$_3$C | 3(R), 3a(S), 7(R) | 107 | +15.5° |
| 11 | | | 3(R), 3a(R), 7(R) | 110 | +69.5° |
| 12 | | | 3(S), 3a(R), 7(R) | 98 | |
| 13 | −CH$_2$OH | OH | 3α, 3aα, 7(R) | 122.5 | |
| 14 | | F$_3$C | 3α, 3aβ, 7(R) | 147.6 | |
| 15 | −CH$_2$OCH$_3$ | OBn | 3α, 3aα, 7(R) | oil | |
| 16 | | | 3α, 3aβ, 7(R) | oil | +115.4° |
| 17 | | | 3(S), 3a(S), 7(R) | oil | +64.8° |
| 18 | | F$_3$C | 3(R), 3a(S), 7(R) | oil | +15.8° |
| 19 | | | 3(R), 3a(R), 7(R) | oil | +61.6° |
| 20 | | | 3(S), 3a(R), 7(R) | oil | |
| 21 | −CH$_2$OCH | OH | 3α, 3aα, 7(R) | 163.4 | |
| 22 | | | 3α, 3aβ, 7(R) | 94.8 | +105.4° |
| 23 | | | 3(S), 3a(S), 7(R) | 120.7–120.9 | +16.7° |
| 24 | | F$_3$C | 3(R), 3a(S), 7(R) | 165.3–165.5 | −35.6° |
| 25 | | | 3(R), 3a(R), 7(R) | 90 | +49.1° |
| 26 | | | 3(S), 3a(R), 7(R) | 103.6–103.8 | |
| 27 | −CH$_2$OCH$_3$ | OH | 3α, 3aβ, 7(S) | 95.5 | −107.0° |
| 28 | | | 3(R), 3a(R), 7(S) | 118.8 | −50.4° |
| 29 | | | 3(R), 3a(S), 7(S) | 103.8–103.9 | −17.5° |
| 30 | | F$_3$C | 3(S), 3a(R), 7(S) | 163.5–163.7 | +33.2° |
| 31 | | | 3(S), 3a(S), 7(S) | oil | |

TABLE-continued

Structure: R₂(R₃)C(R₄)—CH(R₅)—(CH₂)ₙ—O— attached to a 6-position of a tetrahydroquinoline fused with an oxazolidinone (N—C(=O)—O), with —CH₂R₁ substituent on the ring carbon adjacent to N.

| No. | $R_1$ | $R_2(R_3)C(R_4)-CH(R_5)-(CH_2)_n-$ | Config. | m.p. (°C.) | $[\alpha]_D^{20}$ |
|---|---|---|---|---|---|
| 32 | —CH=CH₂ | 1-propyl-1-hydroxycyclopentyl | (cis) (±) | 115 | |
| 33 | | (same) | (trans) (±) | 110 | |
| 34 | —CH₂OH | 1-propyl-1-hydroxycyclopentyl | (cis) (±) | oil | |
| 35 | | (same) | (trans) (±) | oil | |
| 36 | —CH₂OCH₃ | 1-propyl-1-hydroxycyclopentyl | (cis) (±) | 120.6 | |
| 37 | | (same) | (trans) (±) | 129 | |
| 38 | —CH₂OCH₃ | CH₃—CH(OH)—CH₂CH₂CH₃ chain | 3α, 3aα, 7(R) | 70 | |
| 39 | | (same) | 3α, 3aβ, 7(R) | 104 | |
| 40 | —CH₂OH | CH₃—CH(OH)—CH₂CH₂CH₃ chain | 3α, 3aβ, 7(R) | 102 | |
| 41 | —CH=CH₂ | F₃C—CH(OH)—CH₂CH₂CH₂CH₃ | (cis) (±) | 74.4–74.8 | |
| 42 | | | (trans) (±) | 98.2 | +41.1° |
| 43 | | | 3(S), 3a(S) | 68–72 | −34.1° |
| 44 | | | 3(S), 3a(R) | 105 | +31.2° |
| 45 | | | 3(R), 3a(S) | 98–102 | −45.1° |
| 46 | | | 3(R), 3a(R) | 80 | |
| 47 | —CH₂OH | F₃C—CH(OH)—CH₂CH₂CH₂CH₃ | (3α, 3aα) (±) | 138.8 | +56.2° |
| 48 | | | 3(S), 3a(S) | 128 | +12.1° |
| 49 | | | 3(S), 3a(R) | 124 | −12.2° |
| 50 | | | 3(R), 3a(S) | 124 | −57.4° |
| 51 | | | 3(R), 3a(R) | 130 | |
| 52 | —CH₂OCH₃ | F₃C—CH(OH)—CH₂CH₂CH₂CH₃ | (3α, 3aα) (±) | 91 | |
| 53 | | | (3α, 3aβ) (±) | 81 | +72.9° |
| 54 | | | 3(S), 3a(S) | 83.0–83.3 | −16.9° |
| 55 | | | 3(R), 3a(S) | 110.6 | −69.2° |
| 56 | | | 3(R), 3a(R) | 81.6–82.2 | +17.2° |
| 57 | | | 3(S), 3a(R) | 111.0–111.2 | |
| 58 | —CH₂OH | NC—CH₂CH₂CH₂CH₂CH₃ chain | (3α, 3aβ) (±) | 142 | |
| 59 | —CH₂OH | NC—CH₂CH₂CH₂CH₂CH₃ chain | (3α, 3aα) (±) | 95 | |
| 60 | | (same) | (3α, 3aβ) (±) | 65.3 | |
| 61 | —CH₂OCH₃ | F₃C—CH(OH)—CH₂CH₃ | (3α, 3aβ) (±) | 132 | |
| 62 | —CH₂OCH₃ | F₃C—CH(OH)—CH₂CH₃ | (3α, 3aβ) (±) | oil | |
| 63 | H | F₃C—CH(OH)—CH₂CH₂CH₃ | 3a(R, S), 7(R) | 188 | |

TABLE-continued

| No. | $R_1$ | $R_2(R_3)C(R_4)-CH(R_5)-(CH_2)_n-$ | Config. | m.p. (°C.) | $[\alpha]_D^{20}$ |
|---|---|---|---|---|---|
| 64 | H | (propyl chain) | 3a(R, S) | 119.2 | |
| 65 | | $F_3C$–(chain) | 3a(S) | 121.3–121.4 | +33.8° |
| 66 | | | 3a(R) | 121.3 | −31.3° |
| 67 | H | tetrahydropyran-CH₂-CH₂- | 3a(R, S) | 115 | |
| 68 | H | 2-hydroxycyclohexyl-CH₂- | 3a(R, S) | 139 | |
| 69 | H | 1-hydroxycyclopentyl-propyl | 3a(R, S) | 120.9 | |
| 70 | H | NC-(chain) | 3a(R, S) | 113.5–113.6 | |
| 71 | $C_2H_5$ | $F_3C$-CH(OH)-(chain) | 3α, 3aβ, 7(R) | 120–131 | |
| 72 | $C_2H_5$ | $F_3C$-(chain) | trans (±) | 78–82 | |
| 73 | $CH_3$ | $F_3C$-(chain) | trans (±) | 79.1–79.2 | |
| 74 | | $F_3C$-(chain) | cis (±) | 63.9–64.0 | |
| 75 | phenyl | $F_3C$-(chain) | trans (±) | 129.5 | |
| 76 | | $F_3C$-(chain) | cis (±) | 86 | |

The compounds of the invention formed the subject of pharmacological trials which allowed their inhibitory power on monoamine oxidase A and on monoamine oxidase B to be determined.

The MAO-A and MAO-B activities in vitro were measured using a rat brain homogenate as the source of enzyme, according to the method described by C. Fowler and M. Strolin-Benedetti in J. Neurochem., 40, 1534–1541 (1983).

The standard assay consists in homogenizing the rat brain in 20 volumes of 0.1M phosphate buffer (pH=7.4) and in preincubating 100 µl of homogenate (5 mg of tissue) at 37° C. for 20 minutes, in the absence or in the presence of various concentrations of test inhibitor. The reaction is started by the addition of [$^{14}C$]serotonin ([$^{14}C$]5HT, final concentration 125 µM) in order to measure the MAO-A activity or [$^{14}C$]phenylethylamine ([$^{14}C$]PEA, final concentration 8 µM) in order to measure the MAO-B activity, in a final volume of 500 µl. After 5 minutes of incubation for [$^{14}C$]5HT and 1 minute of incubation for [$^{14}C$]PEA, the reaction is stopped by addition of 200 µl of 4N hydrochloric acid. The radioactive metabolites obtained from the oxidative deamination are then separated from the unconverted substrate, by extraction into an organic phase, and are quantified by counting the radioactivity.

The inhibitory activities with respect to MAO-A and to MAO-B are respectively given by the inhibition constants Ki (MAO-A) and Ki (MAO-B).

For the compounds of the invention, the Ki (MAO-A) values range between 0.4 and 28 nM and the Ki (MAO-B) values range between 0.7 and 1000 nM.

Certain compounds of the invention are selective inhibitors of MAO-A, it being possible for the Ki(MAO-B)/Ki (MAO-A) ratio to be between 10 and 1000.

Others are, however, mixed inhibitors of MAO-A and MAO-B, it being possible for the Ki(MAO-B)/Ki(MAO-A) ratio to be between 0.1 and 10.

The inhibitory activity of MAO has also been demonstrated in vivo by the test of the potentiation of L-5-hydroxytryptophan (L-5HTP) in rats, according to the procedure described by M. Jalfre et al. in Arch. Int. Pharmacodyn. 259, 194–221 (1982).

This test is performed under the following conditions: batches of rats (10 for each dose), treated orally with various doses of test product or of vehicle, receive intraperitoneally, 60 minutes later, L-5HTP at a dose of 100 mg/kg, this dose not inducing by itself the serotoninergic syndrome (generalized tremor) in the control animals.

The generalized tremor is classed as all or nothing 30 minutes after administration of the L-5HTP. For each dose of test product, the results are expressed as a percentage of animals exhibiting generalized tremor. The dose which induces tremor in 50% of the animals (ED5o), together with its 95% confidence range, is then calculated from the regression straight line which relates the effect (percentage obtained for each dose) to the logarithm of the dose.

For the compounds of the invention, the $ED_{50}$ ranges between 0.2 and 1.1 mg/kg, thus confirming the inhibitory activity of MAO found in vitro.

Moreover, evaluation of the in-vitro toxicity of the compounds of the invention on hepatocytes from rats and from nonhuman primates after single administration demonstrates a very good tolerance within the concentration range tested (up to 100 μM).

The results obtained show that the compounds of the invention may be used for the preparation of drugs which are selective inhibitors of MAO-A or mixed inhibitors of MAO-A and MAO-B, these drugs finding their therapeutic use in particular in the treatment of depressive states, panic attacks, phobias, anxiety, migraine, cognitive deficiencies linked to age or to dementia and in the prevention and treatment of neurodegenerative diseases such as Parkinson's disease and Alzheimer's disease, and cerebrovascular accidents.

The compounds of the invention may be provided, in combination with excipients, in the form of compositions formulated for the purpose of oral, parenteral or rectal administration, for example in the form of tablets, coated tablets, capsules, solutions, suspensions or suppositories.

Via the oral route, the daily dose of active principle administered may range between 1 and 100 mg/kg, taken as one or more doses. Via the parenteral and rectal routes, it may range between 1 and 100 mg/kg.

Accordingly, the present invention also provides a pharmaceutical composition which comprises a derivative of formula (i) in association with an excipient.

The present invention provides a derivative of formula (I) for use in a method of treatment of the human or animal body.

The present invention further provides the use of a derivative of formula (I) in the manufacture of a medicament for use as a selective inhibitor of MAO-A or a mixed inhibitor of MAO-A and MAO-B.

The derivatives of formula (I) may also be used in a method of treating a subject requiring the administration of a selective inhibitor of MAO-A or a mixed inhibitor of MAO-A and MAO-B which comprises administering to that subject an effective amount of a compound of formula (I).

The present invention further provides a composition which is a selective inhibitor of MAO.-A or a mixed inhibitor of MAO-A and MAO-B comprising a derivative of formula (I) and a pharmaceutically acceptable adjuvant.

Annex 1

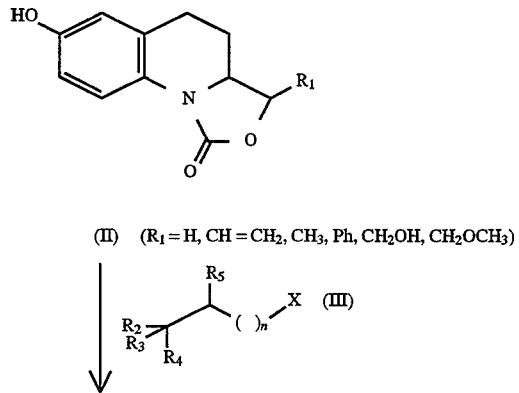

(II)  ($R_1$ = H, CH = $CH_2$, $CH_3$, Ph, $CH_2OH$, $CH_2OCH_3$)

(III)

-continued
Annex 1
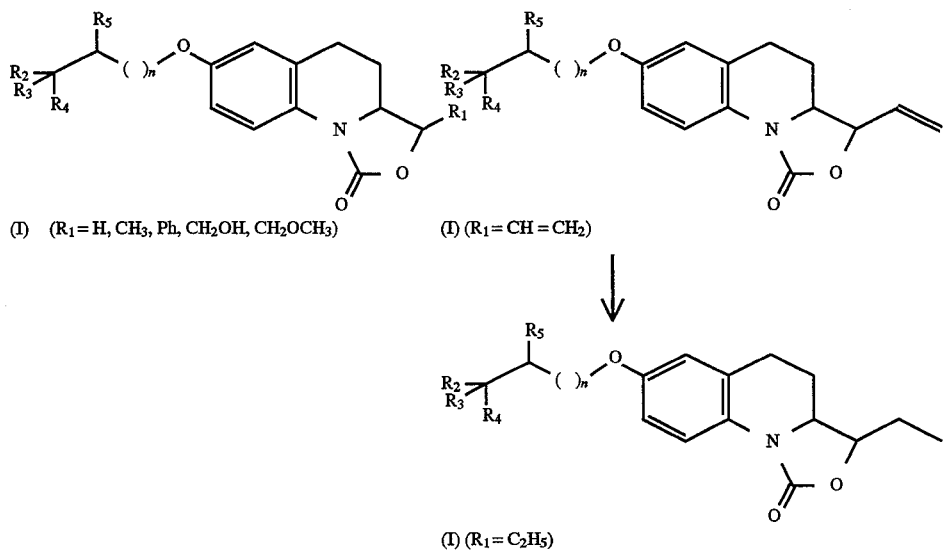
Annex 2
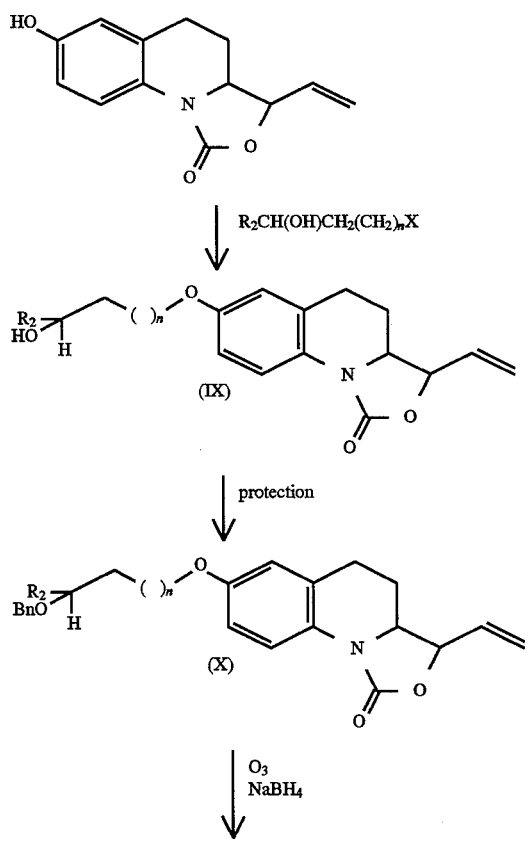

-continued
Annex 2
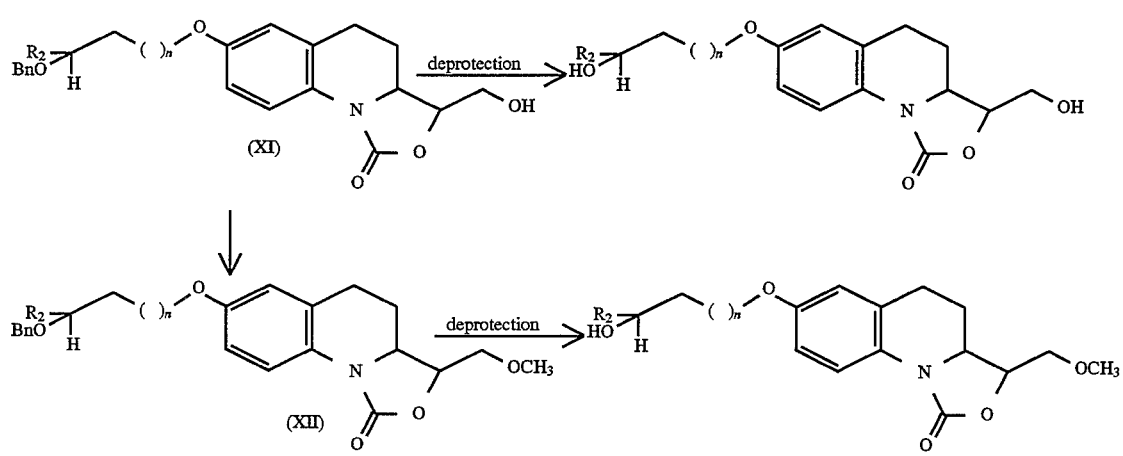
Annex 3
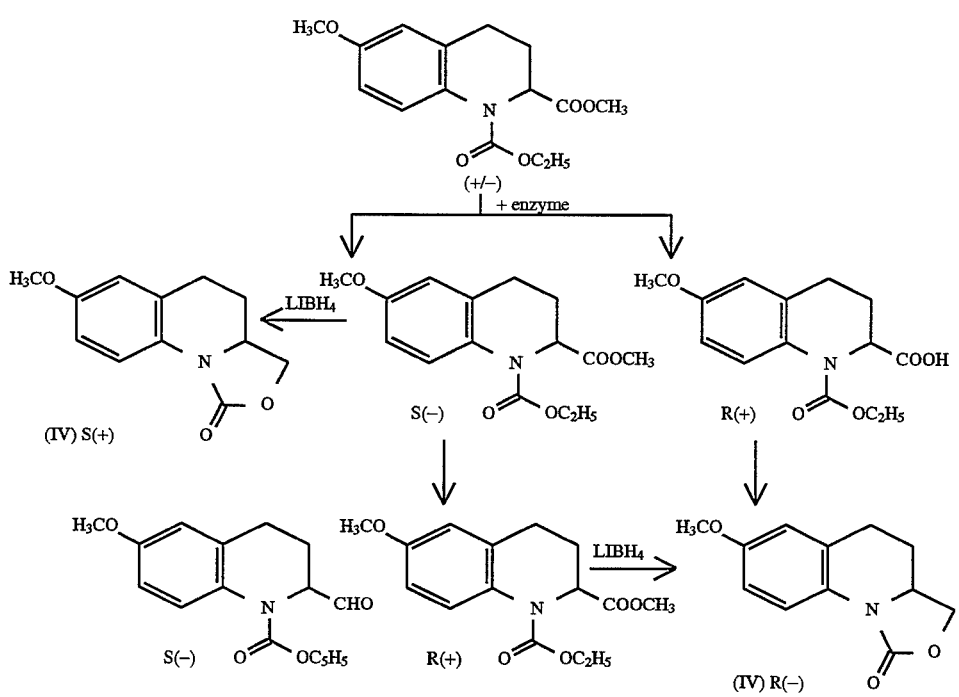

-continued
Annex 3

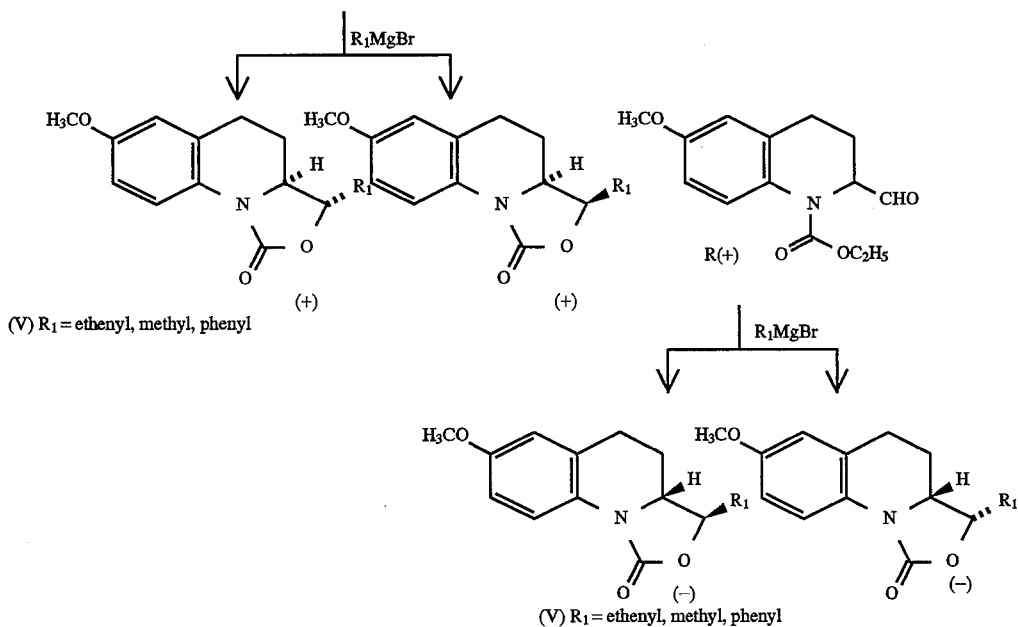

(V) R₁ = ethenyl, methyl, phenyl (V) R₁ = ethenyl, methyl, phenyl

We claim:

1. 3,3a,4,5-tetrahydro-1H-oxazolo[3,4-a]quinolin-1-one derivative which is a compound of formula (I)

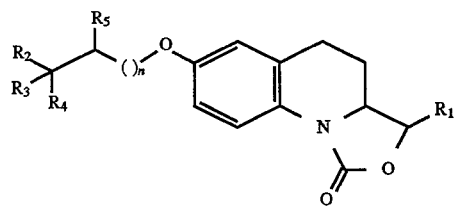

in which:
n is 0 or 1,
R₁ represents a hydrogen atom or an ethenyl, methyl, ethyl, phenyl, hydroxymethyl or methoxymethyl group, and
  (i) R₂ is a methyl, trifluoromethyl or cyano group, R₃ is a hydrogen atom or a hydroxyl or benzyloxy group and R₄ and R₅ are hydrogen atoms, provided if R₂ is methyl, R₃ is not hydrogen,
  or (ii) R₂ and R₄ together form a —(CH₂)₄— group, R₃ is a hydroxyl group and R₅ is a hydrogen atom,
  or (iii) R₂ and R₅ together form an —O—(CH₂)₃— group, and R₃ and R₄ are hydrogen atoms,
  or (iv) R₂ and R₅ together form a —(CH₂)₄ group, R₃ is a hydroxyl group and R₄ is a hydrogen atom, in the form of an isomer or a mixture of isomers.

2. A derivative according to claim 1 which is 3-methoxymethyl-7-(4,4,4-trifluoro-3-hydroxybutoxy)-3,3a,4,5-tetrahydro-1H-oxazolo[3,4-a]quinolin-1-one, 3-methoxymethyl-7-(4,4,4-trifluorobutoxy)-3,3a,4,5-tetrahydro-1H-oxazolo[3,4-a]quinolin-1-one, 7-(4,4,4-trifluorobutoxy)-3,3a,4,5-tetrahydro-1H-oxazolo[3,4-a]quinolin-1-one, 7-(3-hydroxy-4,4,4-trifluorobutoxy)-3,3a,4,5-tetrahydro-1H-oxazolo[3,4-a]quinolin-1-one, or 3-methoxymethyl-7-[(2-(1-hydroxycyclopentyl)ethoxy]-3,3a, 4,5-tetrahydro-1H-oxazolo[3,4-a]quinolin-1-one.

3. Process for the preparation of a derivative of formula (I) as defined in claim 1, in which a compound of formula (II)

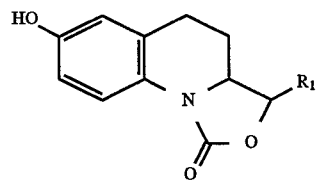

in which R₁ represents a hydrogen atom or an ethenyl, phenyl, hydroxymethyl or methoxymethyl group, is treated with a compound of formula (III)

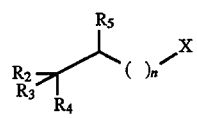

in which R₂, R₃, R₄ and n are defined as in claim 1 and X is a halogen atom or a labile group, to obtain a derivative of formula (I) in which R₁ is defined as above, and, optionally reducing the derivative of formula (I) in which R₁ is an ethenyl group, to obtain a compound of formula (I) in which R₁ is an ethyl group.

4. Process according to claim 3 in which the compound of formula (II) has the same isomeric form as the derivative of formula (I) obtained.

5. Process according to claim 3, in which an enantiomer or diastereoisomer of a compound of formula (II) is prepared from an enantiomer or diastereoisomer of a compound of formula (IV)

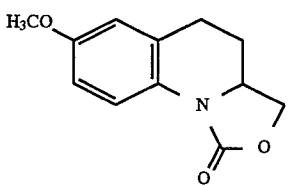

or (V)

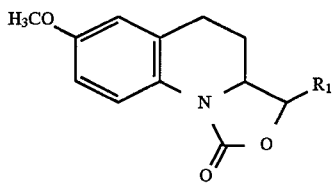

in which $R_1$ represents an ethenyl, methyl or phenyl group, which comprises the enzymatic hydrolysis of ethyl 2-methoxycarbonyl-6-methoxy-1,2,3,4-tetrahydroquinoline-1-carboxylate, followed by the separation by extraction of the S(−) enantiomer of ethyl 2-methoxycarbonyl-6-methoxy-1,2,3,4-tetrahydroquinoline-1-carboxylate from the R(+) enantiomer of ethyl 2-carboxy-6-methoxy-1,2,3,4-tetrahydroquinoline-1-carboxytate, which R(+) enantiomer is treated with thionyl chloride and methanol to give the corresponding 2-methoxycarbonyl derivative; the S(−) and R(+) enantiomers of the 2-methoxycarbonyl derivative are then reacted, with either (i) lithium borohydride, to give the S(+) and R(−) enantiomers respectively of the compound of formula (IV), or (ii) with diisobutylaluminium hydride, to give the S(−) and R(+) enantiomers respectively of the corresponding 2-formyl derivative, which, on treatment with an organomagnesium compound of formula $R_1MgX$, in which $R_1$ is defined as above and X is a halogen atom, and then with sodium methoxide, gives the diastereoisomers of the compounds of formula (V) which are optionally separated by chromatography.

6. Process according to claim 5 in which the enzymatic hydrolysis is carried out using pig liver esterase or horse, pig, bovine, rabbit or sheep liver acetone powders.

7. Pharmaceutical composition which comprises a derivative of formula (I) as defined in claim 1 and an excipient.

8. A method of treating a subject requiring the administration of a selective inhibitor of MAO-A or a mixed inhibitor of MAO-A and MAO-B which comprises administering to that subject an effective amount of a derivative of formula (I) as defined in claim 1.

* * * * *